United States Patent [19]
Harling et al.

[11] Patent Number: 5,773,463
[45] Date of Patent: Jun. 30, 1998

[54] INDANE AND TETRAHYDRONAPHTHALENE DERIVATIVES AS CALCIUM CHANNEL ANTAGONISTS

[75] Inventors: John David Harling; Barry Sidney Orlek, both of Essex, England

[73] Assignee: SmithKline Beecham p.l.c., Brentford, England

[21] Appl. No.: 583,026

[22] PCT Filed: Jul. 21, 1994

[86] PCT No.: PCT/EP94/02409

§ 371 Date: Jan. 22, 1996

§ 102(e) Date: Jan. 22, 1996

[87] PCT Pub. No.: WO95/04028

PCT Pub. Date: Feb. 9, 1995

[30] Foreign Application Priority Data

Jul. 28, 1993 [GB] United Kingdom .................. 9315566

[51] Int. Cl.⁶ ...................... A61K 31/135; C07C 217/52
[52] U.S. Cl. .................. 514/473; 514/351; 514/352; 514/445; 514/447; 514/452; 514/466; 514/469; 514/470; 514/472; 514/524; 514/648; 514/657; 546/300; 546/304; 549/65; 549/68; 549/365; 549/437; 549/466; 549/467; 549/471; 549/479; 549/480
[58] Field of Search ..................................... 564/315, 328, 564/428, 429; 558/418; 549/479; 514/473, 524, 648, 657

[56] References Cited

U.S. PATENT DOCUMENTS

| 4,652,561 | 3/1987 | Mohacsi et al. | 514/211 |
| 4,876,284 | 10/1989 | Arvidsson et al. | 514/657 |
| 4,968,679 | 11/1990 | Junge et al. | 514/222.2 |
| 5,134,168 | 7/1992 | Bitionti et al. | 514/655 |
| 5,149,714 | 9/1992 | Freedman | 514/655 |

FOREIGN PATENT DOCUMENTS

| 0 303 961 | 2/1989 | European Pat. Off. . |
| 0 371 508 | 6/1990 | European Pat. Off. . |
| 2 229 359 | 1/1973 | Germany . |

*Primary Examiner*—Richard L. Raymond
*Attorney, Agent, or Firm*—Linda E. Hall; Stephen A. Venetianer; Edward T. Lentz

[57] ABSTRACT

This invention describes the use of aminoindane and aminotetrahydronaphthalene derivatives of general formula (I)

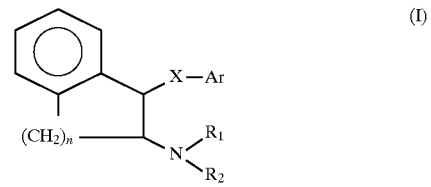

in which Ar, X, $R_1$, $R_2$ and n are defined in claim 1, for the manufacture of a medicament for the treatment of disorders in which a calcium channel antagonist is indicated. Novel compounds falling within formula (I) are also claimed.

17 Claims, No Drawings

INDANE AND TETRAHYDRONAPHTHALENE DERIVATIVES AS CALCIUM CHANNEL ANTAGONISTS

This application is a 371 of PCT/EP94/02409, filed Jul. 21, 1994.

The present invention relates to carbocylic derivatives, processes for their preparation, pharmaceutical compositions containing them and their use in therapy, in particular as calcium channel antagonists, e.g. for the treatment of ischaemic stroke.

Stroke is reportedly the third most common cause of death in the developed world. Current therapies for ischaemic stroke are limited and have a number of disadvantages, such as the risk of exacerbating haemorrhage. There is therefore a need for new and improved treatments for ischaemic stroke.

EPA 303961 describes compounds of the formula

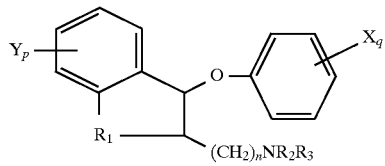

wherein $R_1$ is $C_{1-3}$ alkylene, n and p are each inter alia zero, $R_2$ and $R_3$ represent inter alia hydrogen or lower alkyl, X is inter alia lower alkyl, lower alkoxy, $CF_3$ or halogen and q is zero, 1 or 2. The compounds are said to be useful as antidepressants and as inhibitors of synaptic norepinephrine and serotonin uptake.

EPA 371508 describes similar compounds of the formula:

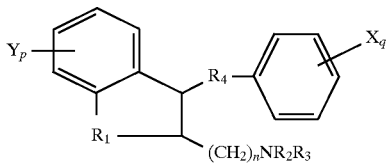

wherein $R_1$, $R_2$, $R_3$, n, p, q and X may have the values recited hereinabove and $R_4$ is oxy or thio, which compounds are said to be useful for the treatment of drug-resistant malaria and other drug-resistant protozoal infections.

We have now found that certain carbocyclic derivatives, such as indanes and tetralins, exhibit activity as calcium channel antagonists.

The present invention therefore provides in a first aspect the use of a compound of formula (I):

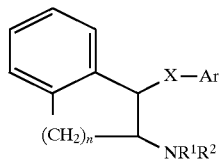

Formula (I)

wherein

X represents O, S or NH;

$R^1$ and $R^2$ each independently represent hydrogen, $C_{1-6}$alkyl, $C_{3-6}$cycloalkyl, or $C_{1-4}$alkyl-$C_{3-6}$cycloalkyl;

n is 1, 2 or 3; and

Ar represents phenyl optionally substituted by 1 to 3 substituents selected from:

halo, $C_{1-4}$alkyl, $C_{1-4}$alkoxy, $C_{1-2}$alkylenedioxy, trifluoromethyl, trifluoromethoxy, CN, $NO_2$, amino, mono- or di-alkylamino, optionally substituted benzoyl and $Ph(CH_2)_rY(CH_2)_s$— where Ph is optionally substituted phenyl, Y is oxygen or a bond and r and s each independently represent 0–4 provided that the sum of r+s is not greater than 4, or Ar represents an optionally substituted unsaturated monocyclic heteroaryl ring system containing 5 or 6 ring members, or an optionally substituted, unsaturated or partially saturated bicyclic aryl or heteroaryl ring system containing 8–10 ring members, or a pharmaceutically acceptable salt thereof, in the manufacture of a medicament for the treatment of disorders wherein a calcium channel antagonist is indicated.

The invention also provides novel compounds of formula (IA):

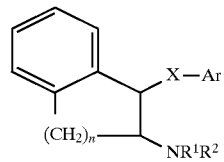

Formula (IA)

wherein

X represents O, S or NH;

$R^1$ and $R^2$ each independently represent hydrogen or $C_{1-6}$allyl;

n is 1, 2 or 3; and

Ar represents phenyl optionally substituted by 1 to 3 substituents selected from:

halo, $C_{1-4}$alkyl, $C_{1-4}$alkoxy, $C_{1-2}$alkylenedioxy, trifluoromethyl, trifluoromethoxy, CN, $NO_2$, amino, mono- or di- alkylamino, optionally substituted benzoyl and $Ph(CH_2)_rY(CH_2)_s$— where Ph is optionally substituted phenyl, Y is oxygen or a bond and r and s each independently represent 0–4 provided that the sum of r+s is not greater than 4, or Ar represents an optionally substituted unsaturated monocyclic heteroaryl ring system containing 5 or 6 ring members, or an optionally substituted, unsaturated or partially saturated bicyclic aryl or heteroaryl ring system containing 8–10 ring members, with the proviso that when X is O or S then Ar is not an unsubstituted phenyl group or phenyl substituted by lower alkyl, lower alkoxy, trifluoromethyl or halogen;

and salts thereof.

In the compounds of formula (I) and formula (IA) when Ar represents phenyl this is advantageously substituted by optionally substituted benzoyl group or a group $Ph(CH_2)_rY(CH_2)_s$— and preferably the group is in the 4- or 3-position, particularly the 4-position. Preferably r and s independently represent zero or 1, such that the sum of r and s does not exceed 1. Suitable substituents for the group Ph and for benzoyl include halogen, $C_{1-4}$alkoxy, $C_{1-4}$alkyl, trifluoromethyl and trifluoromethoxy. Preferably the substituents would be 4-fluoro, 4-chloro, 3-fluoro, 3-chloro or 3,4-dichloro; 4-fluoro is a particularly preferred substituent because this blocks metabolic hydroxylation of the phenyl group. In this sub-group preferably Ar represents phenyl substituted by optionally substituted benzyl, benzyloxy, phenoxy or benzoyl, and preferably the substituent is at the 4-position of the phenyl group. Additionally, in the compounds of formula (I) and the compounds of formula (IA) in which X is nitrogen, Ar is preferably 3,4-dichlorophenyl.

When Ar represents a bicyclic aryl suitable groups include naphthyl.

When Ar represents monocyclic heteroaryl, suitable groups include pyridyl, thienyl and furyl.

When Ar represents bicyclic heteroaryl, suitable groups include benzofuranyl e.g. 5-benzo[b]furanyl.

Suitable substituents for bicyclic aryl and monocyclic and bicyclic heteroaryl groups include halogen, $C_{1-4}$alkyl, $C_{1-4}$alkoxy, trifluoromethyl, trifluoromethoxy, phenyl, phenyl$C_{1-4}$alkyl and phenyl $C_{1-4}$alkoxy.

In a sub-class of compounds at least one of $R^1$ and $R^2$ represents $C_{1-6}$alkyl.

Preferably $R^1$ is methyl, isopropyl or hydrogen, particularly preferably methyl.

Preferably $R^2$ is hydrogen or methyl, particularly preferably hydrogen, so —$NR^1R^2$ is preferably amino, methylamino or isopropylamino.

Preferably X is O or NH, particularly preferably O.

Alkyl groups present in the compounds of formulas (I) and (IA), alone or as part of another group, can be straight or branched. Thus, a $C_{1-6}$alkyl group may be for example methyl, ethyl, n-propyl, n-butyl, n-pentyl, n-hexyl or any branched isomer thereof such as isopropyl or t-butyl. Preferred meanings of $C_{3-6}$cycloalkyl are cyclopropyl and cyclohexyl, and preferred meanings of $C_{1-4}$alkyl-$C_{3-6}$cycloalkyl are cyclopropylmethyl and cyclohexylmethyl.

It will be appreciated that for use in medicine a salt of a compound (I) should be pharmaceutically acceptable. Examples of pharmaceutically acceptable salts include inorganic and organic acid addition salts such as hydrochloride, hydrobromide, sulphate, phosphate, acetate, fumarate, maleate, citrate, lactate, tatrate, oxalate, methanesulphonate or similar pharmaceutically acceptable inorganic or organic acid addition salts. Other non-pharmaceutically acceptable salts may be used for example in the isolation of final products and are included within the scope of this invention.

It will be appreciated that the compounds of formula (I) contain two or more asymmetric centres. Such compounds will exist as optical isomers (enantiomers). Both the pure enantiomers, racemic mixtures (50% of each enantiomer) and unequal mixtures of the two are included within the scope of the invention. Further, all diastereomeric forms possible (pure enantiomers and mixtures thereof) are within the scope of the invention. In particular it will be appreciated that the substituents on the carbocyclic (e.g. indane) nucleus may both lie on the same side with respect to the plane of the ring (cis-configuration) or on opposite sides (trans-configuration). Both forms and all mixtures thereof are included within the scope of this invention.

Preferably the compounds of formula (I) are of the cis-configuration.

In accordance with convention the (+) and (−) designations used herein indicate the direction of rotation of plane-polarised light by the compounds. The prefix (+) indicates that the isomer is dextrorotatory (which can also be designated d) and the prefix (−) indicates the levorotatory isomer (which can also be designated l).

Particular preferred compounds of the formula (I) include:

(±) trans 1-(2-benzylanilino)-2-methylaminoindane,
(±) trans 1-(3,4-dichlorophenylthio)-2-methylaminoindane,
(±)cis-1-(4-benzyloxyphenoxy)-2-methylaminoindane,
(+)cis-1-(4-benzyloxyphenoxy)-2-methylaminoindane,
(−)cis-1-(4-benzyloxyphenoxy)-2-methylaminoindane,
(±)cis-1-[(4-phenoxy)phenoxy]-2-methylaminoindane,
(±)trans-1-(4-benzyloxyphenoxy)-2-methylaminoindane,
(±)cis-1-(4-benzylphenoxy)-2-methylaminoindane,
(±)cis 2-amino-1-(4-benzoylphenoxy)indane,
(±)cis 1-(4-benzoylphenoxy)-2-methylaminoindane,
(±)cis 2-amino-1-(3,4-dichlorophenoxy)indane,
(±)cis 1-(3,4-dichlorophenoxy)-2-dimethylaminoindane,
(±)cis 1-(3,4-dichlorophenoxy)-2-methylaminoindane,
(±)cis 1-[4-(4-fluorophenoxy)phenoxy]-2-methylaminoindane,
(±)cis-1-(4-phenylphenoxy)-2-methylaminoindane,
(±)cis-1-(3-phenylphenoxy)-2-methylaminoindane,
(±)cis-1-(4-tert-butylphenoxy)-2-methylaminoindane,
(±)cis 2-amino-1-[4-(4-fluorophenoxy)phenoxy]indane,
(±)cis-2-amino-1-[4-(4-fluorobenzoyl)phenoxy]indane,
(±)cis-1-[4-(4-fluorobenzoyl)phenoxy]-2-methylaminoindane,
(±) cis 1-[4-(4-fluorophenoxy)phenoxy]-2-isopropylaminoindane, and salts thereof.

The above compounds are believed to be novel and as such represent further embodiments of the invention.

The compounds of the present invention can be prepared by processes analogous to those known in the art. The present invention therefore provides in a further aspect, a process for the preparation of novel compounds of formula (I) which comprises:

(a) to prepare a compound of formula (I) wherein $R^2$ is methyl, reduction of a compound of formula (II)

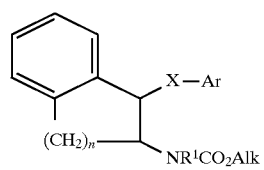

Formula (II)

wherein n, $R^1$, Ar and X are as hereinbefore defined and Alk is a $C_{1-4}$alkyl group;

(b) to prepare a compound of formula (I) wherein at least one of $R^1$ and $R^2$ is hydrogen, deprotection of a compound of formula (II);

(c) reaction of compound of formula (III)

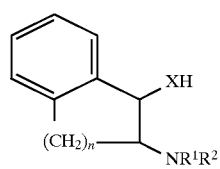

Formula (III)

wherein $R^1$, $R^2$, X and n are as hereinbefore defined with a compound F—Ar, wherein Ar is as hereinbefore defined. This reaction proceeds most readily when the aryl group contains electron-withdrawing substituents e.g. —$CF_3$, 3,4-dichloro, -benzoyl.

(d) reaction of a compound formula (IV):

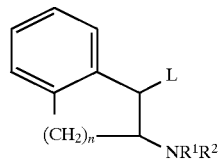

Formula (IV)

wherein $R^1$, $R^2$ and n are as hereinbefore defined and L is a group displaceable by a nucleophile, with a compound HXAr;

(e) interconversion of a compound of formula (I) to a different compound of formula (I), e.g.

(i) where one of $R^1$ and $R^2$ is hydrogen and the other is alkyl, conversion to a compound of formula (I) wherein $R^1$ and $R^2$ are both alkyl, or (ii) where $R^1$ and $R^2$ are both hydrogen, conversion to a compound of formula (I) where at least one of $R^1$ and $R^2$ represent alkyl;

(iii) conversion of a benzoyl substituent in the group Ar to benzyl;

and optionally after any of the above processes, forming a salt of formula (I).

Reduction according to process (a) may be effected using a suitable reducing agent such as lithium aluminium hydride, preferably in an inert solvent such as tetrahydrofuran or diethyl ether.

Deprotection according to process (b) may be carried out by conventional methods. Thus for example an ethoxycarbonyl group may be removed by hydrolysis under basic conditions. A tert-butoxycarbonyl group may be cleaved using trifluoroacetic acid.

In process (c) the reaction between a compound of formula (III) and F—Ar is preferably effected in the presence of a strong base such as sodium hydride, and in a polar organic solvent such as dimethylsulphoxide or dimethylformamide. The aryl group is preferably substituted by an activating group such as benzoyl, or $CF_3$. If necessary during process (c) the nitrogen atom may be protected by methods well known in the art, e.g. a carbamate, which may be removed for example as described in process (b).

Process (d) preferably employs a compound of formula (IV) wherein $R^1$ and $R^2$ are both alkyl, and the reaction with HXAr can take place under conditions which depend on the nature of L and X. For example when L is hydroxy, and X is oxygen or sulphur the reaction is carried out in the presence of diethyl azodicarboxylate and triphenyl phosphine. Such a reaction is known as the Mitsunobu reaction (as described in Synthesis 1981, 1; and J. Org. Chem. 1991, 56, 670–672). Alternatively the leaving group L may be for example a halogen atom or a sulphonyloxy group eg. methane-sulphonyloxy or p-toluene sulphonyloxy, in which case the reaction may be effected using standard conditions in the presence or absence of solvent.

Interconversions according to process (e) may be effected by alkylation of a compound (I) wherein one of $R^1$ and $R^2$ is hydrogen and the other is alkyl or where $R^1$ and $R^2$ are both hydrogen, using an appropriate alkylating agent such as an alkyl halide e.g. an alkyl bromide or iodide, in the presence of a base, such as potassium carbonate. The reaction may be carried out in a suitable solvent such as acetone. Alternatively said compound of formula (I) may first be acylated, using for example an alkylhaloformate such as ethyl chloroformate, preferably in the presence of a tertiary amine such as triethylamine, to provide a compound of formula (II) followed by reduction as described above. In a further method the compound of formula (I) may be subjected to reductive alkylation using an appropriate aldehyde (e.g. formaldehyde) or ketone, and a reducing agent such as sodium cyanoborohydride. Reduction of a benzoyl substituent to benzyl may be effected using e.g. sodium borohydride in trifluoroacetic acid.

It will be appreciated that when any of the processes described herein involve a reduction step it will generally be desirable to employ reducing agents and conditions which do not affect or disturb substituents which are intended to be retained in the final product. The choice of appropriate reducing agents and conditions will be readily apparent to the skilled practitioner. Thus for example when Ar represents 3,4-dichlorophenyl it is preferable to avoid the use of lithium aluminium hydride under forcing (e.g. reflux) conditions.

Processes (a), (b), (c) and (e) generally proceed with retention of the cis or trans configuration of the starting material. Thus the stereochemistry of the final product is usually determined by the configuration of formula (II) which in turn is governed by its method of preparation. For the preparation of trans isomers a compound of formula (II) in which Alk is ethyl is preferably used, and to prepare cis isomers a compound (II) wherein Alk is t-butyl is advantageously employed.

Thus, a trans-compound of formula (II) wherein $R^1$ is hydrogen and Alk is ethyl may be prepared by reacting a compound of formula (V):

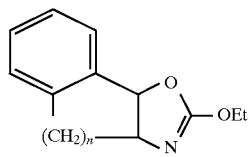

Formula (V)

(wherein n is as hereinbefore defined) with an aryl compound of formula HXAr.

This reaction may conveniently be effected in a solvent such as toluene and in the presence of a catalytic amount of p-toluenesulphonic acid. Compounds of formula HXAr are commercially available or may be prepared by standard methods.

A compound (V) may be prepared from a compound of formula (VI):

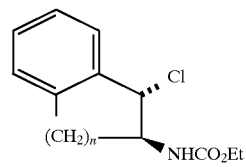

Formula (VI)

by reaction with potassium carbonate or bicarbonate in aqueous ethanol.

Compounds of formula (VI) are known from the literature; see for example J.C.S. Chem Commun. 1980, 462 and European Application No. 88575.

Alternatively a trans-compound of formula (II) wherein X is NH may be prepared directly from a compound of formula (VI) by reaction with a compound Ar—$NH_2$.

A cis-isomer of formula (II) wherein $R^1$ is hydrogen and Alk is tert-butyl may be prepared by reaction of a compound of formula (VII):

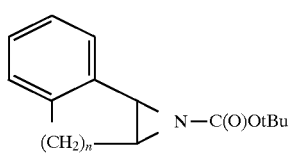

Formula (VII)

with a compound HXAr as defined above. In this reaction X is preferably oxygen.

Compounds of formula (II) (both cis and trans forms) wherein $R^1$ is alkyl may be prepared by alkylation of formula (II) wherein $R^1$ is hydrogen for example using an alkyl halide in the presence of a base such as sodium hydride and in a suitable solvent e.g. dimethylformamide. Alternatively a compound (II) wherein $R^1$ is hydrogen may be reduced as described in process (a) above and subsequently acylated using an alkylhaloformate as described for process (e) above.

A compound of formula (VII) may be prepared by cyclisation of a compound of formula (VIII):

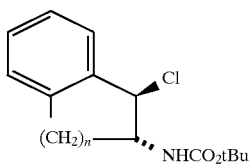

Formula (VIII)

using sodium hydride in a suitable solvent for example an ether such as tetrahydrofuran optionally containing a crown ether such as 15-crown-5; or dimethyl formamide.

Compounds of formula (VIII) may be prepared in a similar manner to compounds of formula (VI), by addition of N,N-dichloro-t-butylcarbamate to an olefin of formula (IX):

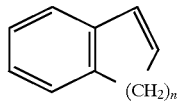

Formula (IX)

Trans-isomers of formula (III) wherein X is oxygen may be prepared as described in the literature e.g. Chem. Pharm. Bull. 1977, 25, 1060. Corresponding cis-isomers may be obtained by oxidation of the trans-isomer using Jones reagent to give a ketone followed by reduction with lithium tri-O-isobutyl borohydride (L-Selectride®, Aldrich). Reduction of the ketone using sodium borohydride regenerates the trans-isomer.

Cis-isomers of Formula (III) in which X is oxygen can be prepared according to the following methods:

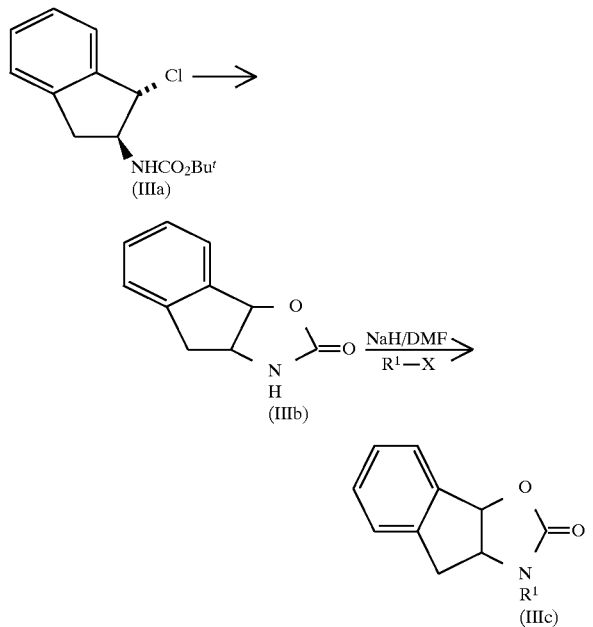

A compound of Formula (IIIa) can be converted into a compound of Formula (IIIb) for example by heating under reflux in chloroform, and the product can be alkylated e.g. by reaction with an alkyl halide and sodium hydride in a suitable dipolar aprotic solvent.

The compounds of Formula (IIIc) can be reduced by lithium aluminium hydride to give compounds of Formula (III) in which $R^2$ is methyl. Compounds of Formula (IIIb) or (IIIc) can be treated with sodium hydroxide to give compounds of Formula (III) in which $R^2$ is hydrogen.

Compounds of Formula (III) in which $R^1$ is methyl and $R^2$ is hydrogen can be prepared by reducing an oxazoline of Formula (IIIe) e.g. with lithium aluminium hydride, which can be prepared from a compound of Formula (IIId):

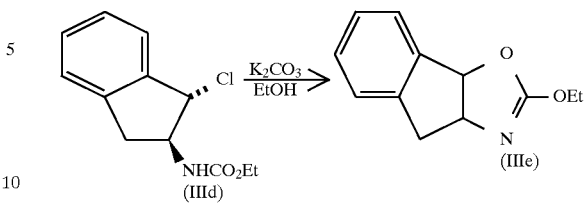

Compounds of formula (III) wherein X is S or NH may be prepared from the corresponding sulphonyloxy compound e.g. a mesylate and an appropriate amino or thiol reagent using standard methods. The sulphonyloxy derivative may itself be prepared from the corresponding alcohol in conventional manner.

Some individual enantiomers of formula (II) are known, e.g. the compound in which X is oxygen, n is 1 and $R^1$ and $R^2$ are both hydrogen (E. J. Corey et al., Tet. Lett. 34, 8399 (1993), G. DeSimoni et al. Gazz. Chim. Ital. 122, 269 (1992), and analogues can be made by appropriate modifications, or by asymmetric synthesis (e.g. see D. E. McClure et al., J.Org.Chem. 48, 2675 (1983)). The use of a resolved enantiomer of Formula III should give rise to a resolved enantiomer of Formula (I).

Compounds of formula (IV) wherein L is OH may be prepared as described for the compounds of formula (III). When L is halogen or a sulphonyloxy group such compounds may be prepared from the corresponding alcohol in conventional manner.

When a compound of formula (I) is obtained as a mixture of enantiomers, these may be separated by conventional methods such as crystallisation in the presence of a resolving agent, or chromatography, for example using a chiral HPLC column.

Preferably the compounds of formula (I) are resolved by conversion to a mixture of diastereomeric amides, which are separated by conventional methods and then reconverted into resolved compounds of formula (I). Preferably the amides are formed with S(+)-α-methoxyphenylacetic acid, and the separated amides can be converted into the resolved amines by treatment with an excess of methyllithium, or by treatment with an excess of potassium t-butoxide in wet tetrahydrofuran as generally described in U.S. Pat. No. 5,149,714.

Compounds of formula (I) have been found to exhibit high calcium influx blocking activity for example in neurons. As such the compounds are expected to be of use in therapy in treating conditions and diseases related to an accumulation of calcium in the brain cells of mammals, in particular humans. For example, the compounds are expected to be of use in the treatment of anoxia, ischaemia including for example stroke, migraine, visceral pain, epilepsy, traumatic head injury, AIDS-related dementia, neuro-degenerative diseases such as Alzheimer's disease and age-related memory disorders, mood disorders and drug addiction withdrawal such as ethanol addiction withdrawal.

In a further aspect of the invention there is therefore provided a method of treatment of conditions or diseases related to (e.g. caused or exacerbated by) the accumulation of calcium in the brain cells of mammals which comprises administering to a subject in need thereof an effective amount of a compound of formula (I) or a pharmaceutically acceptable salt thereof. Thus, for example, the present invention provides a method of treatment of anoxia, ischaemia including for example stroke, migraine, visceral pain, epilepsy, traumatic head injury, AIDS-related dementia, neurodegenerative diseases such as Alzheimer's disease, and age-related memory disorders, mood disorders and drug addiction withdrawal such as ethanol addiction withdrawal, which comprises administering to a subject in need thereof, an effective amount of a compound of formula (I) or a pharmaceutically acceptable salt thereof.

The present invention also provides the use of a compound of formula (I) or a pharmaceutically acceptable salt thereof in the manufacture of a medicament for the treatment of a condition or disease related to the accumulation of calcium in the brain cells of a mammal.

For use in medicine, the compounds of formula (I) are usually administered in a standard pharmaceutical composition. The present invention therefore provides in a further aspect pharmaceutical compositions comprising a novel compound of formula (I) or a pharmaceutically acceptable salt thereof and a pharmaceutically acceptable carrier or excipient.

The compounds of formula (I) may be administered by any convenient method for example by oral, parenteral, buccal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compounds of the invention may also be administered parenterally, by bolus injection or continuous infusion. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Both liquid and solid compositions may contain other excipients known in the pharmaceutical art, such as cyclodextrins.

Preferably the composition is in unit dose form such as a tablet, capsule or ampoule.

Each dosage unit for oral administration contains preferably from 1 to 250 mg (and for parenteral administration contains preferably from 0.1 to 60 mg) of a compound of the formula (I) or a pharmaceutically acceptable salt thereof calculated as the free base.

The daily dosage regimen for an adult patient may be, for example, an oral dose of between 1 mg and 500 mg, preferably between 1 mg and 250 mg, e.g. 5 to 200 mg or an intravenous, subcutaneous, or intramuscular dose of between 0.1 mg and 100 mg, preferably between 0.1 mg and 60 mg, e.g. 1 to 40 mg of the compound of the formula (I) or a pharmaceutically acceptable salt thereof calculated as the free base, the compound being administered 1 to 4 times per day. Alternatively the compounds of the invention may be administered by continuous intravenous infusion, preferably at a dose of up to 400 mg per day. Thus, the total daily dosage by oral administration will be in the range 1 to 2000 mg and the total daily dosage by parenteral administration will be in the range 0.1 to 400 mg. Suitably the compounds will be administered for a period of continuous therapy, for example for a week or more.

BIOLOGICAL DATA $Ca^{2+}$ Current Measurement

Cell Preparations

Sensory neurons from dorsal root ganglia were dissociated from 1 day old rat pups (Forda et al, Developmental Brain Research, 22 (1985), 55–65). Cells were plated out onto glass coverslips and used within 3 days to permit effective voltage clamp of $Ca^{2+}$ currents.

Superior cervical ganglion neurons were isolated and cultured following a method modified from Marrion et al, Neurosci. Lett., 77, 55–60 (1987). Cells were plated onto laminin coated plastic tissue culture dishes and incubated at 37° C. until just prior to recording. Electrophysiological recordings were performed from 2 to 9 days after dissociation.

Solutions

The pipette (internal solution) contained in mM: CsCl, 130; HEPES, 10; EGTA, 10; $MgCl_2$, 4; ATP, 2; buffered to pH 7.2 with CsOH. Cells were bathed in a normal Tyrodes solution before establishment of whole cell recording when the bathing solution was changed to one allowing isolation of $Ca^{2+}$ currents. The external solution for recording $Ca^{2+}$ channel currents contained in mM: $BaCl_2$, 10; TEA-Cl, 130; glucose, 10; HEPES, 10; $MgCl_2$, 1; buffered to pH 7.3 with TEA-OH. Barium was used as the charge carrier as this assists in current isolation and calcium dependent inactivation of current is avoided. Compounds were dissolved in DMSO to make a 20 mM stock solution. At the highest drug concentration used the vehicle (0.1%) had no significant effect on $Ca^{2+}$ currents. All experiments were performed at 21° to 24° C. Whole cell currents were recorded using List EPC-7 amplifiers and stored, digitised for later analysis using PC based software similar to that described previously (Benham & Tsien, Journal of Physiology (1988), 404, 767–784).

Results $Ca^{2+}$ Currents

Peak voltage gated $Ca^{2+}$ channel currents of up to 10 nA were recorded using 10 mM $Ba^{2+}$ as charge carrier. Currents were evoked from a holding potential of −80 mV to a test potential of 0 or +10 mV every 15 seconds. This test potential was at the peak of the current voltage relationship and assessing block at this point reduced any errors due to drifting holding potential. Some cells showed slow rundown of current as is commonly seen when recording $Ca^{2+}$ currents. The rundown rate was measured in control conditions and extrapolated through the time of drug application to derive a rundown corrected control value.

Dorsal Root Ganglion Cells

Block by 20 μM drug was assessed 3 minutes after drug application. Compounds of the invention described in the specific examples gave percentage inhibition of plateau $Ca^{2+}$ current in the range 21–99%.

Superior Cervical Ganglion Cells

Once a constant calcium current had been recorded for 4 successive pulses (1 minute) 10 μM Nimodipine, a dibydropyridine, was applied to the cell to block L type calcium current. After three minutes 5 μM drug was coapplied with 10 μM Nimodipine for three minutes. Such drug application tested the block of the remaining, predominantly N type, calcium current.

Compounds of the invention described in the specific examples gave percentage inhibition of plateau $Ca^{2+}$ current in the range 11 to 98% at 5 μM.

PHARMACEUTICAL FORMULATIONS

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.
Solvent: Typically water but may also include cyclodextrins (1–100 mg) and co-solvents such as propylene glycol, polyethylene glycol and alcohol.

| Tablet | |
|---|---|
| Compound | 1–40 mg |
| Diluent/Filler* | 50–250 mg |
| Binder | 5–25 mg |
| Disintegrant* | 5–50 mg |
| Lubricant | 1–5 mg |
| Cyclodextrin | 1–100 mg |

*may also include cyclodextrins

Diluent: e.g. Microcrystalline cellulose, lactose, starch
Binder: e.g. Polyvinylpyrrolidone, hydroxypropymethylcellulose
Disintegrant: e.g. Sodium starch glycollate, crospovidone
Lubricant: e.g. Magnesium stearate, sodium stearyl fumarate.

| Oral Suspension or Solution | |
|---|---|
| Compound | 1–40 mg |
| Suspending or Solubilising Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose
Solubilising agent: e.g. cyclodextrin
Diluent: e.g. sorbitol solution, typically water
Preservative: e.g. sodium benzoate
Buffer: e.g. citrate
Co-solvent: e.g. alcohol, propylene glycol, polyethylene glycol The invention is further illustrated by the following non-limiting Preparations and Examples:

Preparation 1

(±)cis-2-Ethoxy-3a,8b-dihydro4H-indeno[2,1-d]oxazole

A solution of (±) trans-1-chloro-2-ethoxycarbonylaminoindane (B. J. Walker and P. J. Wrobel, J. Chem. Soc. Chem. Commun., 1980, 462)(4.0 g, 0.017 mol) in ethanol (125 ml) was treated with $K_2CO_3$ (2.4 g, 0.018 mol) and diluted with water (50 ml). After stirring at room temperature for 20 h, the reaction was concentrated under high vacuum to approximately one quarter the original volume, then diluted with water (25 ml) and extracted into diethyl ether (3×50 ml). The combined extracts were washed with brine, dried over $Na_2SO_4$ and concentrated in vacuo to give the title compound as a low melting solid (3.3 g), m.p 53°–54° C. (from diethyl ether/n-pentane).

$^1$H Nmr (CDCl$_3$) δ:1.30 (3H, t, J=7Hz), 3.14 (1H, dd, J=17Hz and J=2Hz), 3.37 (1H, dd, J=17Hz and J=7Hz), 4.20 (1H, dq, J=12Hz and J=7Hz), 4.22 (1H, dq, J=12Hz and J=7Hz), 4.88 (1H, dt, J=7Hz and J=2Hz), 5.93 (1H, d, J=7Hz), 7.20–7.50 (4H, m).

Preparation 2

(±) cis-2-Ethoxy-3a,4,5,9b-tetrahydronapth[2,1-d]oxazole

A solution of (±) trans-1-chloro-2-ethoxycarbonylamino-1,2,3,4-tetrahydronaphthalene (L. M. Gaster and B. S. Orlek, EP 88575)(1.0 g, 4.0 mmol) in ethanol (100 ml) was treated dropwise with a solution of KHCO$_3$ (0.44 g, 4.4 mmol in 30 ml water) over a period of 3 h. After stirring for a further 30 min the reaction was concentrated under high vacuum to approximately one quarter the original volume, then diluted with water and extracted into diethyl ether (3×100 ml). The combined extracts were washed with brine, dried over $Na_2SO_4$ and concentrated in vacua. Flash chromatography on silica gel using petroleum ether 60/80-ethyl acetate as eluant, followed by distillation in a kugelrohr (b.p. 180° C. at 0.4 mmHg) afforded the title compound as a colourless oil (0.69 g).

$^1$H Nmr (CDCl$_3$): 1.33 (3H, t, J=7Hz), 1.95 (2H, m), 2.55 (1H, ddd, J=15.5Hz, J=5Hz and J=5Hz), 2.84 (1H, ddd, J=15.5Hz, J=7Hz and J=7Hz), 4.26 (2H, q, J=7Hz), 4.47 (1H, m), 5.60 (1H, d, J=9Hz), 7.05–7.45 (4H, m).

Preparation 3

(±) 1-Anilino-2-ethoxycarbonylaminoindane

Method A

A solution of (±) trans 1-chloro-2-ethoxycarbonylaminoindane (4.0 g, 0.166 mol) in aniline (25 ml) was heated under nitrogen at 50° C. for 4 h. The reaction was concentrated in vacuo using azeotropic distillation with xylene to remove final traces of aniline. Purification on a silica gel column using a graded eluant of 10–16% ethyl acetate in petroleum ether 40/60 afforded the title compound as colourless solid (3.91 g), m.p. 128°–130° C. (from n-pentane/diethyl ether).

$^1$H Nmr (CDCl$_3$) δ: 1.27 (3H, t, J=7Hz), 2.83 (1H, dd, J=16Hz and J=7Hz), 3.40 (1H, dd, J=16Hz and J=7Hz), 4.12 (3H, m, overlapping signals), 4.36 (1H, m), 4.77 (1H, d, J=6Hz), 5.00 (1H, br s), 6.80 (3H, m), 7.29 (6H, m).

Method B

A solution of (±) cis-2-ethoxy-3a,8b-dihydro-4H-indeno[2,1-d]oxazole (0.41 g, 2.0 mmol) in dry toluene (2 ml) was treated with aniline (0.205 g, 2.2 mmol) and a catalytic amount of p-toluenesulfonic acid monohydrate (10 mg). The mixture was heated under nitrogen at 50° C. for 50 min. The reaction was diluted with diethyl ether (25 ml) and washed with water (3×10 ml) followed by brine (10 ml). The organic phase was dried over Na$_2$SO$_4$ and concentrated in vacuo to give the title compound (0.55 g).

Preparation 4

(±) trans 1-Anilino-2-methylaminoindane

To a stirred suspension of LiAlH$_4$ (1.35 g, 0.035 mol) in dry tetrahydrofuran (25 ml) under nitrogen was added dropwise a solution of (±) trans-1-anilino-2-ethoxycarbonylaminoindane (3.50 g, 0.012 mol) in dry tetrahydrofuran (25 ml). The mixture was heated under reflux for 3.25 h. After cooling in ice, wet diethyl ether was added to quench excess LiAlH$_4$, followed by a minimum amount of water. The precipitate was removed by filtration, and the filtrate was concentrated in vacuo to give a cream coloured solid (2.64 g) which was purified by recrystallisation to give the title compound as a colourless solid, m.p.121°–122° C. (from diethyl ether).

$^1$H Nmr (CDCl$_3$) δ:2.0 (1H, br s), 2.53 (3H, s), 2.74 (1H, dd, J=16Hz and J=7Hz), 3.15–3.40 (2H, m, overlapping signals), 3.92 (1H, br s), 4.81 (1H, br s), 6.75 (3H, m), 7.20 (6H, m).

Preparation 5

(±) trans 1-(2-Benzylanilino)-2-ethoxycarbonylaminoindane

A solution of (±) cis-2-ethoxy-3a,8b-dihydro-4H-indeno[2,1-d]oxazole (2.0 g, 0.01 mol) in dry toluene (15 ml) was treated with 2-benzylaniline (1.83 g, 0.01 mol) and a catalytic amount of p-toluenesulfonic acid monohydrate (50 mg), and the mixture was heated at 60° C. for 1.5 h. The reaction was diluted with diethyl ether, and washed with water followed by brine. The organic phase was dried over Na$_2$SO$_4$ and concentrated in vacuo to give the title compound as a brown foam (3.37 g) which was used in the next stage without purification.

$^1$H Nmr (CDCl$_3$) δ:1.20 (3H, t, J=7Hz), 2.71 (1H, dd, J=16Hz and J=6Hz), 3.13 (1H, dd, J=16Hz and J=7Hz), 3.82 (2H, s), 3.93 (1H, br s), 4.00–4.28 (3H, m), 4.65 (1H, br s), 4.83 (1H, br s), 6.76 (1H, t, J=8Hz), 6.90–7.32 (12H, m).

Preparation 6

(±) trans 1-(Phenoxy)-2-ethoxycarbonylaminoindane

A solution of (±) cis-2-ethoxy-3a,8b-dihydro-4H-indeno[2,1-d]oxazole (1.0 g, 0.005 mol) in dry toluene (7.5 ml) was treated with phenol (0.47 g, 0.005 mol) and a catalytic amount of p-toluenesulfonic acid monohydrate (25 mg). The mixture was heated at 60° C. for 1.5 h and then at 100° C. for 2 h. The reaction was diluted with diethyl ether and washed with saturated NaHCO$_3$ (10 ml) followed by brine (10 ml). The organic phase was dried over Na$_2$SO$_4$ and concentrated in vacuo to give a brown oil (1.47 g) which was purified on a silica gel column using CH$_2$Cl$_2$ as eluant. Pooling of pure fractions afforded the title compound as a colourless solid (0.25 g). Fractions contaminated with phenol were dissolved in diethyl ether and washed with 10% NaOH to give a further 0.25 g of the title compound.

$^1$H Nmr (CDCl$_3$) δ:1.22 (3H, t, J=7Hz), 2.83 (1H, dd, J=17Hz and J=4.5Hz), 3.50 (1H, dd, J=17Hz and J=7Hz), 4.10 (2H, q, J=7Hz), 4.50 (1H,m), 4.88 (1H, br s), 5.56 (1H, m), 6.93–7.47 (9H, m).

Preparation 7

(±) trans 1-(Phenoxy)-2-methylaminoindane

To a stirred suspension of LiAlH$_4$ (0.22 g, 5.7 mmol) in dry diethyl ether (5 ml) under nitrogen was added a solution of (±) trans 1-(phenoxy)-2-ethoxycarbonylaminoindane (0.34 g, 1.14 mmol) in diethyl ether (10 ml). After stirring overnight at room temperature the reaction was worked up as described in Preparation 4 to give the title compound as a brown oil (0.25 g) which was used in the next stage without further purification.

Preparation 8

(±) trans 1-(Phenylthio)-2-ethoxycarbonylaminoindane

A solution of (±) cis-2-ethoxy-3a,8b-dihydro-4H-indeno[2,1-d]oxazole (1.0 g, 0.005 mol) in dry toluene (5 ml) was treated with thiophenol (0.55 g, 0.005 mol) and a catalytic amount of p-toluenesulfonic acid monohydrate (25 mg). The mixture was heated at 60° C. for 2 h and then at 80° C. for a further 5 h. The reaction was diluted with diethyl ether and washed with 5% NaOH (3×10 ml) followed by water (10 ml) and brine (10 ml). The organic phase was dried over Na$_2$SO$_4$ and concentrated in vacuo to give an oil (1.4 g) which was purified on a silica gel column using CH$_2$Cl$_2$ as eluant. Pooling of fractions containing the major slower running component afforded the title compound as a colourless solid (0.74 g), m.p. 60.5°–62° C. (from n-pentane/diethyl ether).

$^1$H Nmr (CDCl$_3$) δ:1.20 (3H, t, J=7Hz), 2.75 (1H, dd, J=17Hz and J=4Hz), 3.42 (1H, dd, J=17Hz and J=6Hz), 4.08 (2H, q, J=7Hz), 4.42 (1H, br s), 4.53 (1H, br s), 4.85 (1H, br s), 7.18–7.50 (9H, m).

Preparation 9

(±) trans 1-(Phenylthio)-2-methylaminoindane

To a stirred suspension of LiAlH$_4$ (0.22 g, 5.7 mmol) in dry diethyl ether (10 ml) under nitrogen was added a solution of (±) trans 1-(phenylthio)-2-ethoxycarbonylaminoindane (0.36 g, 1.15 mmol) in diethyl ether (15 ml). After stirring overnight at room temperature the reaction was worked up as described in Preparation 4 to give the title compound as a brown oil (0.27 g) which was used in the next stage without purification.

Preparation 10

(±) trans 1-(3,4-Dichlorophenylthio)-2-ethoxycarbonylaminoindane

A solution of (±) cis-2-ethoxy-3a,8b-dihydro-4H-indeno [2,1-d]oxazole (0.61 g, 3.0 mmol) in dry toluene (15 ml) was treated with 3,4-dichlorothiophenol (0.59 g, 3.3 mmol) and a catalytic amount of p-toluenesulfonic acid (0.15 ml of an anhydrous 0.1M solution of p-toluenesulfonic acid in benzene). The mixture was heated under nitrogen at 70°–75° C. for 3.5 h. The reaction was diluted with diethyl ether and washed with 5% NaOH (3×10 ml) followed by water (10 ml) and brine (10 ml). The organic phase was dried over $Na_2SO_4$ and concentrated in vacuo to give a solid (1.0 g). Purification on a silica gel column using $CHCl_3$ as eluant afforded the title compound as a colourless solid (0.81 g).

$^1$H Nmr (CDCl$_3$) δ:1.21 (3H, t, J=7Hz), 2.77 (1H, dd, J=17Hz and J=4Hz), 3.42 (1H, dd, J=17Hz and J=6.5Hz), 4.10 (2H, q, J=7Hz), 4.42 (1H, br s), 4.59 (1H, s), 4.87 (1H, br s), 7.20–7.40 (6H, m), 7.56 (1H, d, J=2Hz).

Preparation 11

(±) trans 1-(2-Benzylanilino)-2-(N-methyl-N-ethoxycarbonylamino)indane

A solution of (±) trans 1-(2-benzylanilino)-2-methylaminoindane (Example 2)(0.66 g, 2.0 mmol) in dry diethyl ether (25 ml) was treated with triethylamine (0.55 ml, 4.0 mmol) and ethyl chloroformate (0.21 ml, 2.2 mmol). After stirring at room temperature for 1 h, the reaction was concentrated in vacuo and the residue was partitioned between chloroform (25 ml) and water (25 ml). The organic layer was washed with water (3×25 ml) followed by brine (25 ml), and then concentrated in vacuo to give a brown oil (0.73 g) which crystallised on cooling and was used in the next stage without purification.

$^1$H Nmr (CDCl$_3$) (57° C.) δ:1.19 (3H, br t, J=7Hz), 2.80 (3H, s), 3.02 (2H, m), 3.86 (2H, ABq, J=16Hz), 3.93 (1H, br s), 4.10 (2H, q, J=7Hz), 4.58 (1H, m), 5.02 (1H, br t), 6.70–7.28 (13H, m).

Preparation 12

(±) trans 1-(2-Naphthalenethio)-2-ethoxycarbonylaminoindane

A solution of (±) cis-2-ethoxy-3a,8b-dihydro-4H-indeno [2,1-d]oxazole (0.41 g, 2.0 mmol) in dry toluene (15 ml) was treated with 2-naphthalenethiol (0.35 g, 2.2 mmol) and a catalytic amount of p-toluenesulfonic acid (0.1 ml of an anhydrous 0.1M solution of p-toluenesulfonic acid in benzene).The mixture was heated under nitrogen at 75° C. for 3 h and then at 80°–90° C. for 12 h. The reaction was worked up as described in Preparation 10 to give an oil (0.7 g). Purification on a silica gel column using 20% diethyl ether in petroleum ether 40/60 as eluant afforded the title compound as a gum (0.42 g) which was triturated with n-pentane/diethyl ether to give a colourless solid, m.p. 85°–86.5° C.

$^1$H Nmr (CDCl$_3$) δ:1.18 (3H, br s), 2.76 (1H, dd, J=16Hz and J=3Hz), 3.43 (1H, dd, J=16Hz and J=6Hz), 4.05 (2H, br q), 4.52 (1H,br s), 4.69 (1H, br s), 4.89 (1H, br s), 7.15–8.10 (11H, m).

Preparation 13

(±) trans 1-(4-Benzoylanilino)-2-ethoxycarbonylaminoindane

A solution of (±) cis-2-ethoxy-3a,8b-dihydro-4H-indeno [2,1-d]oxazole (2.50 g, 0.012 mol) in dry toluene (40 ml) was treated with 4-aminobenzophenone (2.43 g, 0.012 mol) and a catalytic amount of p-toluenesulfonic acid (0.25 ml of an anhydrous 0.1M solution of p-toluenesulfonic acid in benzene). The mixture was heated under nitrogen at 80° C. overnight. The reaction was worked up as described in Preparation 5. Purification on a silica gel column using a graded eluant of 5–40% ethyl acetate in petroleum ether 40/60 afforded the title compound as a yellow foam (3.65 g).

$^1$H Nmr (CDCl$_3$) δ:1.20 (3H, t, J=8Hz), 2.85 (1H, dd, J=17Hz and J=7Hz), 3.37 (1H, dd, J=17Hz and J=7Hz), 4.11 (2H, q, J=8Hz), 4.37 (1H, m), 4.82 (1H, d, J=6Hz), 5.03 (1H, br d, J=7Hz), 6.81 (2H, d, J=8Hz), 7.15–7.90 (12H, m).

Preparation 14

(±) trans 1-(3,4-Dichloroanilino)-2-ethoxycarbonylaminoindane

A solution of (±) cis-2-ethoxy-3a,8b-dihydro-4H-indeno [2,1-d]oxazole (1.0 g, 0.005 mol) in dry toluene (20 ml) was treated with 3,4-dichloroaniline (0.81 g, 0.005 mol) and a catalytic amount of p-toluenesulfonic acid (5 ml of an anhydrous 0.1M solution of p-toluenesulfonic acid in benzene). The mixture was heated under nitrogen at 60° C. for 3 h. The reaction was worked up as described in Preparation 5. Purification on a silica gel column using 1% ethanol in chloroform as eluant afforded the title compound as a solid (1.33 g).

$^1$H Nmr (CDCl$_3$) δ:1.20 (3H, t, J=7Hz), 2.80 (1H, dd, J=16Hz and J=6Hz), 3.33 (1H, dd, J=16Hz and J=6Hz), 4.11 (2H, q, J=7Hz), 4.29 (2H, m), 4.67 (1H, t, J=6Hz), 4.93 (1H, br d), 6.63 (1H, m), 6.88 (1H, d, J=3Hz), 7.23 (5H, m).

Preparation 15

(±) trans 1-(2-Benzylanilino)-2-ethoxycarbonylamino-1,2,3,4-tetrahydronaphthalene A solution of (±) cis-2-ethoxy-3a,4,5,9b-tetrahydronapth [2,1-d]oxazole (1.90 g, 8.76 mmol) in dry toluene (15 ml) was treated with 2-benzylaniline (1.60 g, 8.76 mmol) and a catalytic amount of p-toluenesulfonic acid (0.5 ml of an anhydrous 0.1M solution of p-toluenesulfonic acid in benzene). The mixture was heated at 50° C. for 1.5 h. The reaction was worked up as described in Preparation 5. Trituration with n-pentane afforded the title compound as a pale yellow solid (2.47 g).

$^1$H Nmr (CDCl$_3$) δ:1.20 (3H, br m), 1.73 (2H, m), 2.72 (2H, m), 3.73 (1H, m), 3.76 (2H, s), 4.10 (3H, m), 4.39 (1H, br s), 4.65 (1H, br d), 6.73 (1H, t, J=7Hz), 6.92–7.33 (12H, m).

Preparation 16

(±)trans-1-Chloro-2-tert-butoxycarbonylaminoindane

To a solution of indene (32.58 g, 0.28 mol) in toluene (350 ml) under nitrogen was added dropwise a solution of N,N-dichloro-t-butylcarbamate (60 g, 0.323 mol) in toluene (200 ml). The solution was then stirred at 50° C. for 5 h. Saturated aqueous sodium metabisulfite (500 ml) was then added with cooling from an external ice/water bath. The two phase mixture was then vigorously stirred at room temperature for 3 h. The phases were then separated and the aqueous phase extracted with diethyl ether (3×100 ml). The organic phases were then combined and washed successively with saturated aqueous sodium bicarbonate, water and brine. After drying over $Na_2SO_4$, solvents were removed in vacuo to afford the title compound as a white solid (71.60 g).

$^1$H Nmr ($CDCl_3$) δ:1.47 (9H, s), 2.80 (1H, dd, J=7,15Hz), 3.52 (1H, dd, J=7,15Hz), 4.47 (1H, m), 4.78 (1H, m), 5.19 (1H, br. s), 7.27 (3H, m),7.42 (1H, m).

Preparation 17

(±) N-tert-butoxycarbonyl-1,2-iminoindane

To a suspension of NaH (80% disp. in oil, 2.016 g, 67.2 mmol) in dry tetrahydrofuran (300 ml) was added (±)trans-1-chloro-2-tert-butoxycarbonylaminoindane (15 g, 56 mmol) and 15-crown-5 (50 μl). The mixture was then warmed at 50° C. under nitrogen for 18 h after which it was poured into water (700 ml) and extracted with diethyl ether (3×150 ml). The combined organic extracts were dried ($Na_2SO_4$) and solvents were removed in vacuo to afford the title compound as a brown solid (12.67 g).

$^1$H Nmr ($CDCl_3$) δ:1.08 (9H, s), 3.04 (1H, dd, J=5,18Hz) ,3.50 (2H,m), 3.84 (1H, m), 7.20 (3H, d, J=4Hz), 7.46 (1H, m).

Preparation 18

(±)cis-1-(2-Benzylphenoxy)-2-tert-butoxycarbonylaminoindane

A solution of (±) N-tert-butoxycarbonyl-1,2-iminoindane (2.33 g, 10 mmol), 2-hydroxy diphenylmethane (1.84 g, 10 mmol) and pyridinium p-toluenesulfonate (50 mg) in chloroform (100 ml) was heated at reflux for 3 h. On cooling, the solution was washed sequentially with aq. $NaHCO_3$, water and then brine. After drying over $Na_2SO_4$, solvents were removed in vacuo and the resultant brown oil subjected to column chromatography on silica gel eluting with 10% diethyl ether in hexanes to afford a pale yellow oil which was a mixture of the desired adduct and the starting phenol. This mixture was taken up in 1:1 diethyl ether:pentane (200 ml) and washed three times with a 1:1 mixture of methanol and 10% aq. NaOH. After washing with water then brine, the organics were dried over $Na_2SO_4$ and then concentrated in vacuo. The residue was recrystallised to afford the title compound as a white solid (1.03 g) m.p. 113°–114.5° C. (from diethyl ether-pentane).

$^1$H Nmr ($CDCl_3$) δ:1.38 (9H, s), 2.87 (1H, dd, J=7,15Hz), 3.18 (1H, dd, 7,15Hz), 3.72 (1H, d, 15Hz), 3.81 (1H, d, 15Hz), 4.60 (1H, m), 4.80 (1H, d, 9Hz), 5.59 (1H, d, 5Hz), 6.88–7.34 (13H, m).

Preparation 19

(±)cis-1-(2-Benzylphenoxy)-2-(N-methyl-N-tert-butoxycarbonylamino)indane

To a suspension of sodium hydride (80% disp. in oil, 43 mg, 1.4 mmol) in dry N,N-dimethylformamide (2 ml) under nitrogen was added dropwise a solution of (±)cis-1-(2-benzylphenoxy)-2-tert-butoxycarbonylaminoindane (492 mg, 1.2 mmol) in dimethylformamide (5 ml). After stirring the mixture for 45 minutes at room temperature, iodomethane (88 μl, 1.4 mmol) was added dropwise and stirring continued for a further 45 minutes. The reaction mixture was then poured into a large excess of water and extracted with diethyl ether (3×30 ml). The combined organic extracts were dried over $Na_2SO_4$ and concentrated in vacuo. The residue was subjected to column chromatography on silica gel eluting with 10% diethyl ether in hexanes to afford the title compound as a colourless oil (477 mg).

$^1$H Nmr ($CDCl_3$) δ:1.37 (9H, s), 2.45+2.57 (3H, br.s+br.s, rotamers), 3.16 (2H, d, J=6Hz), 3.86 (2H, d, 6Hz), 5.13+5.35 (1H, m+m, rotamers), 5.22 (1H, d, J=7Hz), 6.82–7.37 (13H, m).

Preparation 20

(±)cis-1-(4Benzyloxyphenoxy)-2-tert-butoxycarbonylaminoindane

The title compound was prepared in a similar manner to Preparation 18 from (±) N-tert-butoxycarbonyl-1,2-iminoindane (5 g, 21.6 mmol), 4-benzyloxyphenol (4.3 g, 21.6 mmol), pyridinium p-toluenesulfonate (100 mg) and chloroform (150 ml). After a reaction time of 3 h, the reaction was diluted with chloroform (100 ml) then washed sequentially with water and brine. After drying over sodium sulfate, volatiles were removed in vacuo and the residue subjected to column chromatography on silica gel eluting with 10% diethyl ether in hexanes to afford a light brown solid which was recrystallised to afford the title compound (3.6 g) as a white solid. (from diethyl etherhexanes).

$^1$H Nmr ($CDCl_3$) δ:1.44 (9H, s), 3.04 (1H, dd, 7,15Hz), 3.27 (1H, dd, J=7,15Hz), 4.63 (1H, m), 5.03 (2H, s), 5.29 (1H, d, J=9Hz), 5.43 (1H, d, J=6Hz), 6.91 (4H, m), 7.13–7.46 (9H, m).

Preparation 21

(±)cis-1-(4Benzyloxyphenoxy)-2-(N-methyl-N-tert-butoxycarbonylamino)indane

The title compound was prepared in a similar manner to Preparation 19 from sodium hydride (80% disp. in oil, 83 mg, 2.76 mmol) in dry N,N-dimethylformamide (5 ml), (±)cis-1-(4-benzyloxy phenoxy)-2-tert-butoxycarbonylaminoindane (1 g, 2.3 mmol) in N,N-dimethylformamide (5 ml) and iodomethane (175 μl, 2.76 mmol). Column chromatography on silica gel eluting with a gradient of 10–15% diethyl ether in hexanes afforded the title compound (968 mg) as a colourless oil.

$^1$H Nmr ($CDCl_3$) δ:1.36 (9H,s), 2.72 (3H, br. s), 3.21 (2H, m), 5.03 (2H, s), 5.27 (1H, s), 5.63 (1H, m), 6.93 (4H, m), 7.17–7.51 (9H, m).

Preparation 22

(±)cis-1-[5-(2-Phenylbenzo[b]furanyloxy)]-2-tert-butoxycarbonylandnoindane

The title compound was prepared in a similar manner to Preparation 18 from (±)N-tert-butoxycarbonyl-1,2-iminoindane (2.77 g, 12 mmol), 5-hydroxy-2-phenylbenzo [b]furan (2.5 g, 11.9 mmol), pyridinium p-toluenesulfonate (50 mg) and chloroform (100 ml). After a reaction time of 2.5 h, the reaction was diluted with chloroform (100 ml) then washed sequentially with saturated aq. sodium bicarbonate, water and brine. After drying over $Na_2SO_4$, volatiles were removed in vacuo and the residue subjected to column chromatography on neutral alumina eluting with dichloromethane to afford the title compound (2.44 g) as an oil.

$^1$H Nmr ($CDCl_3$) δ:1.44 (9h, s), 3.09 (1H, dd, J=7,15Hz), 3.30 (1H, dd, 6,15Hz), 44.69 (1H, m), 5.33 (1H, d, J=9Hz), 5.56 (1H, d, J=6Hz), 6.92 (2H, m), 7.11–7.51 (9H, m), 7.84 (2H, d, J=8Hz).

Preparation 23

(±)cis-1-[(4-Phenoxy)phenoxy]-2-tert-butoxycarbonylaminoindane

The title compound was prepared in a similar manner to Preparation 18 from (±) N-tert-butoxycarbonyl-1,2-iminoindane (3 g, 13 mmol), 4-phenoxyphenol (2.42 g, 13 mmol), pyridinium p-toluenesulfonate (50 mg) and chloroform (100 ml). After a reaction time of 3 h, the reaction was diluted with chloroform (100 ml) then washed sequentially with saturated aq. sodium bicarbonate, water and brine. After drying over $Na_2SO_4$, volatiles were removed in vacuo and the residue subjected to column chromatography on neutral alumina eluting with 10% diethyl ether in hexanes to afford the title compound (2.16 g) as a foam.

$^1$H Nmr (CDCl$_3$) δ:1.44 (9H, s), 3.06 (1H, dd, J=7,15Hz), 3.29 (1H, dd, 6,15Hz), 4.66 (1H, m), 5.25 (1H, d, J=9Hz), 5.52 (1H, d, J=6Hz),6.90–7.42 (13H, m).

Preparation 24

(±)trans-1-(4-Benzyloxyphenoxy)-2-ethoxycarbonylaminoindane (±) cis-2-Ethoxy-3a,8b-dihydro-4H-indeno[2,1-d]oxazole (2.2 g, 10.8 mmol), 4-benzyloxyphenol (2.17 g, 10.8 mmol), p-toluenesulfonic acid (40 mg) were dissolved in toluene (50 ml) and heated at 60° C. for 5 h, then 2 h at reflux under nitrogen. On cooling, the reaction mixture was diluted with diethyl ether (150 ml) and washed sequentially with 10% aq. sodium hydroxide, water and brine. After drying over sodium sulfate, solvents were removed in vacuo and the residue subjected to column chromatography on silica gel eluting with 20% diethyl ether in hexanes to afford the title compound (1.17 g) as a foam.

$^1$H Nmr (CDCl$_3$) δ:1.22 (3H, t, J=7Hz), 2.80 (1H, dd, J=7,16Hz), 3.50 (1H, dd, J=7,16Hz), 4.12 (2H, q, J=7Hz), 4.50 (1H, m), 4.78 (1H, m), 5.02 (2H, s), 5.45 (1H, br. s), 6.88–7.49 (13H, m).

Preparation 25

(±)cis-1-(4-Benzylphenoxy)-2-tert-butoxycarbonylaminoindane

The title compound was prepared in a similar manner to Preparation 18 from (±)N-tert-butoxycarbonyl-1,2-iminoindane (2 g, 8.7 mmol), 4-benzylphenol (1.59 g, 8.7 mmol), pyridinium p-toluenesulfonate (30 mg) and chloroform (50 ml). After a reaction time of 3 h, the reaction was diluted with chloroform (50 ml) then washed sequentially with saturated aq. sodium bicarbonate, water and brine. After drying over $Na_2SO_4$, volatiles were removed in vacuo and the residue subjected to column chromatography on neutral alumina eluting with 10% diethyl ether in hexanes to afford the title compound (1.4 g) as a foam $^1$H Nmr (CDCl$_3$) δ:1.40 (9H, s), 3.04 (1H, dd, J=7,15Hz), 3.26 (1H, dd, 7,15Hz), 3.93 (2H, s), 4.63 (1H, m), 5.21 (1H, d, J=9Hz), 5.55 (1H, d, J=6Hz), 6.93 (2H, d, J=9Hz), 7.10 (2H, d, J=9Hz),7.13–7.35 (9H, m).

Preparation 26

2-Phenyl-5-hydroxybenzo[b]furan

A solution of 2-phenyl-5-methoxybenzo[b]furan (K K Thomas and M M Bokadia, J Indian Chem. Soc. 1966, 43, 713) (0.5 g, 2.23 mmol) in absolute chloroform (4 ml) was treated with trimethylsilyl iodide (0.44 ml, 3.09 mmol) and warmed at 50° C. for 48 h. A further quantity (0.22 ml) of trimethylsilyl iodide was added during this period. The reaction mixture was diluted with methanol (20 ml), treated with brine (40 ml) and extracted into diethyl ether (2×40 ml). The combined extracts were washed with aqueous sodium metabisulphite, followed by brine (40 ml) and dried over sodium sulphate. After concentration in vacuo the residue was distilled to give the title compound as a colourless solid (0.41 g, 88%) b.p. 250° C., 0.1 mm Hg (Kugelrohr).

Preparation 27

(±) cis 3,3a,4,8b-Tetrahydroindeno[2,1-d]oxazol-2-one

A solution of (±) trans-1-chloro-2-tert-butoxycarbonylaminoindane (10.0 g, 0.037 mol) in chloroform (200 ml) was heated under reflux in an argon atmosphere for 23 h. The mixture was concentrated in vacuo to give a brown solid. Trituration with diethyl ether afforded the title compound as a beige solid (6.0 g, 92%) m.p. 205°–206° C. which was used without further purification.

$^1$H Nmr (CDCl$_3$) δ:3.10 (1H, d, J=17Hz), 3.30 (1H, dd, J=17Hz and J=6.4Hz), 4.68 (1H, t, J=6.4Hz), 5.98 (1H, d, J=7.5Hz), 6.15 (1H, br s), 7.22–7.48 (3H, m), 7.50 (1H, d, J=7Hz).

Preparation 28

(±) cis 2-Amino-1-indanol

A suspension of (±) cis 3,3a,4,8b-tetrahydroindeno[2,1-d]oxazol-2-one (Preparation 27) (5.73 g, 0.033 mol) in a mixture of ethanol (100 ml) and water (20 ml) was treated with sodium hydroxide pellets (8.0 g, 0.2 mol). After stirring at room temperature until the sodium hyroxide pellets had dissolved the mixture was heated under reflux in an argon atmosphere for 5 h. The solution was concentrated in vacuo to approximately one quarter the original volume then diluted with brine (50 ml) and extracted into chloroform (3×100 ml). The combined organic extracts were dried over $Na_2SO_4$ and then concentrated in vacuo to give a brown solid (4.74 g) which was crystallised from i-propanol-diethyl ether to give the title compound as a colourless solid (3.5 g, 72%) m.p. 104.5°–106° C. Mother liquors afforded a further 0.41 g, m.p. 103.5°–105° C.

$^1$H Nmr (CDCl$_3$): 2.28 (3H, br s), 2.75 (1H, dd, J=15.8Hz and J=5.1Hz), 3.12 (1H, dd, J=15.8Hz and J=6.6Hz), 3.70 (1H, br m), 4.80 (1H, d, J=5.4Hz), 7.20 (3H, m), 7.40 (1H, m).

Preparation 29

(±) cis 2-Methylamino-1-indanol

Method A

To a suspension of (±) cis 3,3a,4,8b-tetrahydroindeno[2,1-d]oxazol-2-one (Preparation 27) (3.80 g, 21.71 mmol) in dry tetrahydrofuran (25 ml) was added a solution of LiAlH$_4$ (2.28 g, 60 mmol) in dry tetrahydrofuran. The mixture was heated under reflux for 5.5 h in an argon atmosphere. The reaction was quenched with wet diethyl ether followed by a minimum amount of water. After filtration through Kieselguhr the precipitate was washed with 5% methanol in diethyl ether. The combined filtrate and washings were concentrated in vacuo to give a brown oil (3.35 g). Purification on a short alumina column eluting with 2–30% methanol in chloroform afforded the title compound as an oil (1.87 g) which crystallised on standing.

$^1$H Nmr (CDCl$_3$) δ:2.48 (3H, s), 2.80 (overlapping signals: 1H, dd, J=15.5Hz and 6.7Hz; 1H, br s, exchanges with D$_2$O), 3.05 (1H, dd, J=15.5Hz and 6.9 Hz), 3.30 (1H, q, J=6.8Hz), 4.85 (1H, d, J=5.5Hz), 7.22 (3H, m), 7.45 (1H, m).

Method B

To a suspension of LiAlH$_4$ (4.56 g, 0.12 mol) in dry tetrahydrofuran (50 ml) was added a solution of (±) cis-2-ethoxy-3a,8b-dihydro-4H-indeno[2,1-d]oxazole (8.12 g, 0.04 mol) (Preparation 1) in dry tetrahydrofuran (100 ml). The reaction was stirred at room temperature under an argon atmosphere for 24 h. The reaction was quenched with wet diethyl ether followed by a minimum amount of water. After filtration through Kieselguhr the precipitate was washed with 5% methanol in diethyl ether. The combined filtrate and washings were concentrated in vacuo to give the title compound as a brown solid (6.18 g, 95%) which was used without further purification.

Preparation 30

(±)cis-1-Phenoxy-2-tert-butoxycarbonylaminoindane

The title compound was prepared in a similar manner to Preparation 18 from (±) N-tert-butoxycarbonyl-1,2-iminoindane (3 g, 13 mmol), phenol (1.22 g, 13 mmol), pyridinium p-toluenesulfonate (50 mg) and chloroform (100 ml). After a reaction time of 3 h, the reaction was diluted with chloroform (100 ml) then washed sequentially with saturated aq. sodium bicarbonate, water and brine. After drying over sodium sulfate, volatiles were removed in vacuo and the residue subjected to column chromatography on silica gel eluting with 10% diethyl ether in hexanes to afford a light brown solid which was recrystallised to afford the title compound (3.6 g) as a white solid m.p. 99°–101° C. (from diethyl ether-hexanes).

$^1$H Nmr (CDCl$_3$) δ:1.41 (9H, s), 3.06 (1H, dd, J=7 and J=15Hz), 3.28 (1H, dd, J=6Hz and J=15Hz), 4.68 (1H, m), 5.23 (1H, m), 5.60 (1H, d, J=6Hz), 7.00 (3H, m), 7.19 (1H, m), 7.38 (5H, m).

Preparation 31

(±)cis-1-(4-Phenylphenoxy)-2-tert-butoxycarbonylaminoindane

A solution of (±) N-tert-butoxycarbonyl-1,2-iminoindane (5 g, 22 mmol), 4-phenylphenol (3.73 g, 22 mmol) and pyridinium p-toluenesulfonate (108 mg) in chloroform (150 ml) was heated at reflux for 2 h. On cooling, the solution was washed sequentially with 10% aq. NaOH, water and then brine. After drying over MgSO$_4$, solvents were removed in vacuo and the resultant brown oil subjected to column chromatography on silica gel eluting with 20% diethyl ether in hexanes to afford the title compound (2.95 g).

$^1$H Nmr (CDCl$_3$) δ:1.43 (9H, s), 3.07 (1H, dd, J=7,15Hz), 3.29 (1H, dd, 7,15Hz), 4.70 (1H,m), 5.25 (1H, d, J=9Hz), 5.65 (1H, d, J=7Hz), 7.10 (2H, d, J=9Hz), 7.17–7.58 (11H, m).

Preparation 32

(±)cis-1-(3-Phenylphenoxy)-2-tert-butoxycarbonylaminoindane

A solution of (±) N-tert-butoxycarbonyl-1,2-iminoindane (5 g, 22 mmol), 3-phenylphenol (3.75 g, 22 mmol) and pyridinium p-toluenesulfonate (114 mg) in chloroform (150 ml) was heated at reflux for 2 h. On cooling, the solution was washed sequentially with 10% aq. NaOH, water and then brine. After drying over MgSO$_4$, solvents were removed in vacuo and the resultant brown oil subjected to column chromatography on silica gel eluting with 20% diethyl ether in hexanes to afford the title compound (3.11 g).

$^1$H Nmr (CDCl$_3$) δ:1.40 (9H, s), 3.07 (1H, dd, J=7,15Hz), 3.30 (1H, dd, J=7,15Hz), 4.70 (1H, m), 5.26 (1H, d, J=9Hz), 5.67 (1H, d, J=7Hz), 7.02–7.13 (1H, m), 7.20–7.46 (10H, m), 7.59 (2H, d, J=7Hz).

Preparation 33

(±)cis-1-(4-tert-Butylphenoxy)-2-tert-butoxycarbonylaminoindane

A solution of (±) N-tert-butoxycarbonyl-1,2-iminoindane (5 g, 22 mmol), 4-tert-butylphenol (3.34 g, 22 mmol) and pyridinium p-toluenesulfonate (109 mg) in chloroform (150 ml) was heated at reflux for 2 h. On cooling, the solution was washed sequentially with 10% aq. NaOH, water and then brine. After drying over MgSO$_4$, solvents were removed in vacuo and the resultant brown oil subjected to column chromatography on silica gel eluting with 20% diethyl ether in hexanes to afford the title compound (1.42 g).

$^1$H Nmr (CDCl$_3$) δ:1.31 (9H, s), 1.41 (9H, s), 3.06 (1H, dd, J=7,15Hz), 3.28 (1H, dd, J=7,15Hz), 4.68 (1H, m), 5.24 (1H, d, J=9Hz), 5.59 (1H, d, J=7Hz), 6.97 (2H, d, J=9Hz), 7.18–7.36 (6H, m).

EXAMPLE 1

(±) trans 1-Anilino-2-(N-methyl-N-pentylamino) indane Hydrochloride (E1)

A solution of (±) trans 1-anilino-2-methylaminoindane (0.30 g, 1.26 mmol) in acetone (10 ml) containing K$_2$CO$_3$ (0.19 g, 1.39 mmol) was treated with 1-bromopentane (0.17 ml, 1.39 mmol) and refluxed for 4 days. During this period a further portion of 1-bromopentane (0.17 ml) was added. After evaporation of solvent the the residue was treated with water and extracted into diethyl ether. The organic layers were dried over Na$_2$SO$_4$ and concentrated in vacuo. Purification on a silica gel column using 1% methanol in chloroform as eluant afforded an oil (0.27 g) which was extracted into n-pentane and treated with ethereal hydrogen chloride to give the title compound as a colourless solid, m.p. 202°–204° C. (from methanol/diethyl ether).

$^1$H Nmr (free base)(CDCl$_3$) δ:0.88 (3H, t, J=7Hz), 1.28 (4H, m), 1.48 (2H, m), 2.28 (3H, s), 2.50 (2H, t, J=7Hz), 2.93 (1H, dd, J=16Hz and J=8Hz), 3.02 (1H, dd, J=16Hz and J=7Hz), 3.95 (1H, br d, J=7Hz), 4.90 (1H, t, J=7Hz), 6.76 (3H, m), 7.10–7.35 (6H, m).

EXAMPLE 2

(±) trans 1-(2-Benzylanilino)-2-methylaminoindane Hydrochloride (E2)

To a suspension of LiAlH$_4$ (1.6 g, 42.75 mmol) in dry diethyl ether (100 ml) was added a solution of (±) trans 1-(2-benzylanilino)-2-ethoxycarbonylaminoindane (3.3 g, 8.55 mmol) in diethyl ether (50 ml). After stirring at room temperature for 22 h, the reaction was quenched with wet diethyl ether followed by a minimum amount of water. The reaction was filtered and then concentrated in vacuo to give an oil which crystallised on cooling. After purification on a silica gel column, using diethyl ether as eluant, the product was extracted into pentane and treated with ethereal hydrogen chloride to give the title compound as a colourless solid, m.p. 203°–205° C. (dec.)(from methanol/diethyl ether).

$^1$H Nmr (DMSO-$d_6$) δ:2.45 (3H, s), 3.14 (1H,dd, J=16Hz and J=9Hz), 3.35 (1H, dd, J=16Hz and J=7Hz), 3.88–4.05 (3H, m, overlapping signals), 5.55 (1H, t, J=8Hz), 5.63 (1H, d, J=8Hz), 6.60 –7.35 (13H, m), 9.68 (1H, br s).

EXAMPLE 3

(±) trans 1-(2-Benzylanilino)-2-(N-methyl-N-pentylamino)indane Hydrochloride (E3)

A solution of (±) trans 1-(2-benzylanilino)-2-methylaminoindane (0.98 g, 3.0 mmol) in acetone (30 ml) was treated with 1-iodopentane (0.4 ml, 3.0 mmol) and $K_2CO_3$, and refluxed for 32 h. During this period a further portion of 1-iodopentane (0.1 ml) was added. The reaction was worked up as described for Example 1 and purified on a silica gel column using 0–1% ethanol in chloroform as eluant to give an oil (0.93 g). The product was extracted into n-pentane and treated with ethereal hydrogen chloride to give the title compound as a colourless solid, m.p. 173°–175° C. (from methanol/diethyl ether).

$^1$H Nmr (free base)(CDCl$_3$) δ:0.88 (3H, t, J=7Hz), 1.25 (4H, m), 1.40 (2H, m), 2.10 (3H, s), 2.36 (2H, m), 2.90 (2H, d, J=8Hz), 3.20 (2H, q, J=6Hz), 3.82 (3H, m, overlapping signals), 4.82 (1H, t, J=6Hz), 6.65–7.30 (13H, m).

EXAMPLE 4

(±) trans 1-Phenoxy-2-(N-methyl-N-pentylamino) indane Hydrochloride (E4)

A solution of (±) trans 1-phenoxy-2-methylaminoindane (0.25 g, 1.0 mmol) in dry acetone (10 ml) containing $K_2CO_3$ (0.14 g, 1.0 mmol) was treated with 1-iodopentane (0.2 ml, 1.5 mmol) and refluxed overnight. The reaction was worked up as described for Example 1 and then purified on a silica gel column using 0.5% ethanol in dichloromethane as eluant to give an oil (0.15 g). The product was extracted into n-pentane and treated with ethereal hydrogen chloride to give the title compound as a colourless solid, m.p. 134°–136° C. (from acetone/diethyl ether).

$^1$H Nmr (free base)(CDCl$_3$) δ:0.87 (3H, t, 7Hz), 1.26 (4H, m), 1.50 (2H, m), 2.27 (3H, s), 2.49 (2H, t, J=7Hz), 2.96 (1H, dd, J=16Hz and J=7Hz), 3.15 (1H, dd, J=16Hz and J=7Hz), 3.63 (1H, m), 5.72 (1H, d, J=5Hz), 6.95–7.40 (9H, m).

EXAMPLE 5

(±) trans 1-(Phenylthio)-2-(N-methyl-N-pentylamino)indane Hydrochloride (E5)

A solution of (±) trans 1-(phenylthio)-2-methylaminoindane (0.27 g, 1.05 mmol) in dry acetone (10 ml) was treated with 1-iodopentane (0.17 ml, 1.27 mmol) and $K_2CO_3$ (0.15 g, 1.05 mmol), and refluxed under nitrogen for 22 h. The reaction was worked up as described for Example 1, and the crude product was purified on a silica gel column using 0.5% ethanol in chloroform as eluant to give an oil (0.14 g). The product was extracted into n-pentane and treated with ethereal hydrogen chloride to give the title compound as a colourless solid, m.p. 164°–165.5° C. (from acetone/diethyl ether).

$^1$H Nmr (free base)(CDCl$_3$) δ:0.88 (3H, t, J=7Hz), 1.10–1.47 (6H, m), 2.06 (3H, s), 2.30 (2H, m), 2.88 (1H, dd, J=16Hz and J=3Hz), 3.11 (1H, dd, J=16Hz and J=7Hz), 3.68 (1H, m), 4.67 (1H, d, J=3Hz), 7.12–7.50 (9H, m).

EXAMPLE 6

(±) trans 1-(3,4-Dichlorophenylthio)-2-methylaminoindane Hydrochloride (E6)

To a suspension of LiAlH$_4$ (0.34 g, 9.05 mmol) in dry diethyl ether under nitrogen was added a solution of (±) trans 1-(3,4-dichlorophenylthio)-2-ethoxycarbonylaminoindane (0.69 g, 1.81 mmol) in diethyl ether. After stirring at room temperature overnight, the reaction was worked up as described for Example 2, and then purified on a silica gel column using 1% ethanol in chloroform as eluant. The resulting oil (0.26 g) was extracted into n-pentane and treated with ethereal hydrogen chloride to give the title compound as a colourless solid, m.p. 143°–144° C. (from methanol/diethyl ether).

$^1$H Nmr (DMSO-$d_6$) δ:2.62 (3H, s), 3.15–3.45 (2H, m), 3.97 (1H, m), 5.41 (1H, m), 7.30–7.90 (7H,m), 9.80 (2H, br s).

EXAMPLE 7

(±) trans 1-(2-Benzylanilino)-2-N,N-dimethylaminoindane Hydrochloride (E7a) and (±) cis 1-(2-Benzylanilino)-2-N,N-dimethylaminoindane Hydrochloride (E7b)

Method A

To a suspension of LiAlH$_4$ (0.26 g, 6.88 mmol) in dry diethyl ether (20 ml) under nitrogen was added a solution of (±) trans 1-(2-benzylanilino)-2-(N-methyl-N-ethoxycarbonylamino)indane (0.55 g, 1.38 mmol) in dry tetrahydrofuran (10 ml). After stirring at room temperature overnight, the reaction was worked as described for Example 2. The resulting brown oil contained two basic products as judged by thin layer chromatography (silica gel: 1% ethanol in chloroform). The mixture was separated on a silica gel column using 0.5–1% ethanol in chloroform as eluant. Pooling of fractions containing the more mobile component afforded a pale yellow oil (0.13 g) which was extracted into n-pentane and treated with ethereal hydrogen chloride to give (±) cis 1-(2-benzylanilino)-2-N,N-dimethylamninoindane hydrochloride (E7a) as a colourless solid, m.p. 267°–270° C. (dec)(from methanol/diethyl ether).

$^1$H Nmr (free base)(CDCl$_3$) δ: 2.00 (6H, s), 2.80–3.10 (3H, m, overlapping signals), 3.86 (2H, ABq, J=15.5Hz), 4.62 (1H, br d), 5.38 (1H, br s), 6.70 (1H, t, J=7Hz), 6.95–7.50 (12H, m).

Pooling of fractions containing the less mobile component afforded a pale yellow oil (0.15 g) which was treated with ethereal hydrogen chloride to give (±) trans 1-(2-benzylanilino)-2-N,N-dimethylaminoindane hydrochloride (E7b) as a colourless solid m.p. 222°–223° C. (dec)(from methanol/diethyl ether).

$^1$H Nmr (free base)(CDCl$_3$) δ:2.13 (6H, s), 2.80–3.07 (3H, m, overlapping signals), 3.84 (3H, m, overlapping signals), 4.86 (1H, t, J=7Hz), 6.73 (1H, t, J=8Hz), 6.90–7.30 (12H, m).

Method B

A solution of (±) trans 1-(2-benzylanilino)-2-methylaminoindane (0.10 g, 0.30 mmol) in dry acetone (4 ml) was treated with iodomethane (47 mg, 0.33 mmol) and $K_2CO_3$ (41 mg, 0.30 mmol), and stirred overnight at room temperature. A further portion of iodomethane (24 mg) was added, and stirring was continued overnight. The reaction was concentrated in vacuo, and the residue was partitioned between diethyl ether and water. The aqueous layer was further extracted with diethyl ether, and the combined organic layers were dried over $Na_2SO_4$, and concentrated in vacuo to give an oil (50 mg) which was shown by $^1H$ Nmr to be identical to (±) trans 1-(2-benzylanilino)-2-N,N-dimethylaminoindane (E7b) obtained in Method A.

EXAMPLE 8

(±) trans 1-(2-Benzylanilino)-2-(N-methyl-N-ethylamino)indane hydrochloride (E8)

A solution of (±) trans 1-(2-benzylanilino)-2-methylaminoindane (0.275 g, 0.84 mmol) in dry acetone was treated with iodoethane (0.16 g, 1.0 mmol) and $K_2CO_3$ (0.14 g, 1.0 mmol), then refluxed for 18 h. During this period a further portion of iodoethane (0.026 g) was added. The reaction was concentrated in vacuo, diluted with water and extracted with a mixture of ethyl acetate and diethyl ether. Purification by chromatography on a silica gel column using 1% ethanol in chloroform as eluant afforded a gum (0.29 g) which was extracted into n-pentane and treated with ethereal hydrogen chloride to give the title compound as a colourless solid, m.p. 186°–187.5° C. (from methanol/diethyl ether).

$^1H$ Nmr (free base)($CDCl_3$) δ:0.98 (3H, t, J=7Hz), 2.09 (3H, s), 2.40 (2H, m), 2.91 (2H, m), 3.17 (1H, q, J=7Hz), 3.83 (3H, m, overlapping signals), 4.86 (1H, t, J=7Hz), 6.70–7.30 (13H, m).

EXAMPLE 9

(±) trans 1-(2-Naphthylthio)-2-methylaminoindane Hydrochloride (E9)

(±) trans 1-(2-Naphthylthio)-2-ethoxycarbonylaminoindane (0.31 g, 0.86 mmol) was reduced with $LiAlH_4$ (0.33 g, 8.6 mmol) as described for Example 2. After stirring at room temperature for 24 h, the reaction was worked up as described for Example 2. Purification on a silica gel column using 1% ethanol in chloroform as eluant afforded an oil (0.14 g) which was extracted into n-pentane and treated with ethereal hydrogen chloride to give the title compound as a colourless solid, m.p. 196°–197.5° C. (dec.)(from methanoildiethyl ether).

$^1H$ Nmr (DMSO-$d_6$) δ:2.51 (3H, s), 3.17 (1H, dd, J=18Hz and J=5Hz), 3.32 (1H, dd, J=18Hz and J=7Hz), 3.90 (1H, m), 5.38 (1H, d, J=5Hz), 7.20–8.25 (11H, m), 9.73 (2H, s).

EXAMPLE 10

(±) trans 1-(4-Benzylanilino)-2-methylaminoindane (E10)

(±) trans 1-(4-Benzoylanilino)-2-ethoxycarbonylaminoindane (1.0 g, 2.50 mmol) was reduced with $LiAlH_4$ (0.95 g, 25.0 mmol) as described for Example 2. After stirring at room temperature for 2 days, the reaction was worked up as described for Example 2. Purification on a silica gel column using 0–2% ethanol in chloroform as eluant afforded a solid (0.58 g) which was recrystallised to give the title compound as a colourless solid, m.p. 137°–138° C. (from methanol/diethyl ether/n-pentane).

$^1H$ Nmr ($CDCl_3$) δ:1.60 (1H, br s), 2.52 (3H, s), 2.72 (1H, dd, J=15Hz and J=6Hz), 3.25 (2H, m, overlapping signals), 3.82 (1H, br d), 3.90 (2H, s), 4.78 (1H, br m), 6.69 (2H, d, J=8Hz), 7.02 (2H, d, J=–8Hz), 7.10–7.36 (9H, m).

EXAMPLE 11

(±) trans 1-(3,4-Dichloroanilino)-2-methylaminoindane Hydrochoride (E11)

(±) trans 1-(3,4-Dichloroanilino)-2-ethoxycarbonylaminoindane (0.73 g, 2.0 mmol) was reduced with $LiAlH_4$ (0.38 g, 10.0 mmol) as described for Example 2. After stirring at room temperature for 24 h, the reaction was worked up as described for Example 2. Purification on silica gel using 0–2% ethanol in chloroform afforded a solid (0.23 g) which was treated with ethereal hydrogen chloride to give the title compound as a colourless solid, m.p. 189°–191° C. (from acetone/diethyl ether).

$^1H$ Nmr (DMSO-$d_6$) δ:2.76 (3H, s), 3.23 (1H, dd, J=15.5 and J=7Hz), 3.50 (1H, dd, J=15.5Hz and J=7Hz), 3.92 (1H, m), 5.57 (1H, t, J=7Hz), 6.80–7.60 (8H, m), 9.84 (2H, br s).

EXAMPLE 12

(±)cis-1-(2-Benzylphenoxy)-2-methylaminoindane Hydrochloride (E12)

To a solution of $LiAlH_4$ (436 mg, 12 mmol) in dry tetrahydrofuran (30 ml) under nitrogen was added dropwise a solution of (±)cis-1-(2-benzylphenoxy)-2-tert-butoxycarbonylaminoindane (500 mg, 1.2 mmol) in dry tetrahydrofuran (10 ml). The reaction was heated at reflux for 2 h then cooled with an ice/water bath and quenched with the minimum of water. The reaction was filtered and dried over $Na_2SO_4$. Solvents were removed in vacuo and the residue subjected to column chromatography on silica gel eluting with 5% ethanol in chloroform to afford a colourless oil (356 mg,) which was converted to the HCl salt and crystallised to afford the title compound as a white solid. m.p. 191°–193° C. (from acetonediethyl ether).

$^1H$ Nmr ($CDCl_3$) δ:2.57 (3H,s), 3.25 (2H, d, J=8Hz), 3.66 (1H, d, J=15Hz), 3.83 (1H, m) 3.90 (1H, d, J=15Hz), 5.88 (1H, d, J=6Hz), 6.80–7.40 (13H, m), 9.31 (1H, br, s), 9.67 (1H, br. s).

EXAMPLE 13

(±)cis-1-(2-Benzylphenoxy)-2-dimethylaminoindane Hydrochloride (E13)

The title compound was prepared in a similar manner to Example 12 from $LiAlH_4$ (401 mg, 10.6 mmol), cis-1-(2-benzylphenoxy)-2-(N-methyl-N-tert-butoxycarbonylamino) indane (453 mg, 1.06 mmol) and tetrahydrofuran (50 ml). After a reaction time of 3 h the reaction was worked up as previously described and subjected to column chromatography on silica gel eluting with 5% ethanol in chloroform to afford a pale green oil (331 mg) which was converted to the HCl salt and crystallised to afford the title compound as a white solid. m.p. 222°–225° C. (from methanol-diethyl ether).

$^1H$ Nmr ($CDCl_3$) δ:2.52+2.55 (3H, s+s, mixture of protomers), 2.75+2.77 (3H, s+s, mixture of protomers), 3.32 (1H, dd, J=7,16Hz), 3.57 (1H, dd, J=7,16Hz), 3.68 (1H, d, J=15Hz), 3.92 (1H, d, J=15Hz), 4.05 (1H, m), 5.93 (1H, d, J=7Hz), 6.85 (2H, m), 6.94–7.38 (11H, m), 12.57 (1H, br. s).

EXAMPLE 14

(±)cis-1-(4-Benzyloxyphenoxy)-2-Methylaminoindane Hydrochloride (E14)

The title compound was prepared in a similar manner to Example 12 from $LiAlH_4$ (760 mg, 20 mmol), (±) cis-1-(4- benzyloxyphenoxy)-2-tert-butoxycarbonylaminoindane (1 g, 2.3 mmol) and tetrahydrofuran (50 ml). After a reaction time of 4 h the reaction was worked up as previously described and subjected to column chromatography on silica gel eluting with 5% ethanol in chloroform to afford a pale yellow oil (765 mg) which was converted to the HCl salt and crystallised to afford the title compound as a white solid. m.p. >195° C. dec.(from methanol-diethyl ether).

$^1$H Nmr (DMSO-d$_6$) δ:2.78 (3H, s), 3.39 (2H, m), 4.14 (1H, m), 5.15 (2H, s), 5.96 (1H, d, J=7Hz), 7.07 (2H, d, J=9Hz), 7.20 (2H, d, J=9Hz), 7.25–7.63 (9H,m), 9.70 (2H, br. s).

EXAMPLE 15

(±)cis-1-(4-Benzyloxyphenoxy)-2-dimethylaminoindane Hydrochloride (E15)

The title compound was prepared in a similar manner to Example 12 from LiAlH$_4$ (769 mg, 20.2 mmol), cis-1-(4-benzyloxyphenoxy)-2-(N-methyl-N-tert-butoxycarbonylamino)indane (900 mg, 2.02 mmol) and tetrahydrofuran (50 ml). After a reaction time of 3 hours the reaction was worked up as previously described and subjected to column chromatography on silica gel eluting with 5% ethanol in chloroform to afford a pale green oil (640 mg) which was converted to the HCl salt and crystallised to afford the title compound as a white solid. m.p. 215°–216° C. dec. (from methanol-diethyl ether).

$^1$H Nmr (DMSO-d$_6$) δ:2.93 (6H, s), 3.36 (4H, m), 4.17 (1H, br. s), 5.06 (2H, m), 5.86 (1H,d, J=7Hz), 6.96 (1H, d, J=9Hz), 7.02 (1H, d, J=9Hz), 7.05–7.54 (9H, m), 10.50 (1H, br. s).

EXAMPLE 16

(±)cis-1-[5-(2-Phenylbenzo[b]furanyloxy)]-2-methylaminoindane Hydrochloride (E16)

The title compound was prepared in a similar manner to Example 12 from LiAlH$_4$ (646 mg, 17 mmol), (±) cis-1-[5-(2-phenylbenzo[b]furanyloxy)]-2-tert-butoxycarbonylaminoindane (750 mg, 1.7 mmol) and tetrahydrofuran (40 ml). After a reaction time of 3 h the reaction was worked up as previously described and subjected to column chromatography on silica gel eluting with 2% ethanol in chloroform to afford a colourless oil (556 mg) which was converted to the HCl salt and crystallised to afford the title compound as a white solid. m.p. >230° C. dec. (from methanol-diethyl ether).

$^1$H Nmr (DMSO-d$_6$) δ:2.73 (3H, s), 3.38 (2H, m), 4.13 (1H, q, J=7Hz), 5.87 (1H, d, J=7Hhz), 7.05–7.66 (11H, m), 7.93 (2H, d, J=8Hz), 9.14 (2H, br. s).

EXAMPLE 17

(±)cis-1-[(4-Phenoxy)phenoxy]-2-methylaminoindane Hydrochloride (E17)

The title compound was prepared in a similar manner to Example 12 from LiAlH$_4$ (760 mg, 20 mmol), (±)cis-1-[(4-phenoxy)phenoxy]-2-tert-butoxycarbonylaminoindane (1.39 mg, 3.3 mmol) and tetrahydrofuran (40 ml). After a reaction time of 3 h the reaction was worked up as previously described and subjected to column chromatography on silica gel eluting with 2% ethanol in chloroform to afford a pale pink oil (951 mg) which was converted to the HCl salt and crystallised to afford the title compound as a white solid. m.p. 188°–190° C. (from methanol-diethyl ether).

$^1$H Nmr (DMSO-d$_6$) δ:2.67 (3H, s), 3.31 (2H, m), 4.09 (1H, q, J=7Hz), 5.86 (1H, d, J=7Hz), 6.90–7.47 (13H, m), 9.59 (2H, br. s).

EXAMPLE 18

(±)trans-1-(4-Benzyloxyphenoxy)-2-methylaminoindane Hydrochloride (E18)

The title compound was prepared in a similar manner to Example 12 from LiAlH$_4$ (190 mg, 5 mmol), trans-1-(4-benzyloxyphenoxy)-2-ethoxycarbonylaminoindane (750 mg, 1.7 mmol) and tetrahydrofuran (50 ml). After a reaction time of 18 h at room temperature and a further hour at reflux, the reaction was worked up as previously described and subjected to column chromatography on silica gel eluting with 2% ethanol in chloroform to afford a pale yellow oil (290 mg) which was converted to the HCl salt and crystallised to afford the title compound as a white solid. m.p. 185°–187° C. (from methanol-diethyl ether).

$^1$H Nmr (DMSO-d$_6$) δ:2.61 (3H, s), 3.11 (1H, dd, J=7, 15Hz), 3.41 (1H, dd, J=7,15Hz), 4.00 (1H, q, J=7Hz), 5.09 (2H, s), 6.18 (1H, d, J=7Hz), 6.96–7.52(13H, m), 9.80 (2H, br. s).

EXAMPLE 19

(±)cis-1-(4-Benzylphenoxy)-2-methylaminoindane Hydrochloride (E19)

The title compound was prepared in a similar manner to Example 12 from LiAlH$_4$ (320 mg, 8.4 mmol), cis-1-(4-benzylphenoxy)-2-tert-butoxycarbonylaminoindane (700 mg, 1.7 mmol) and tetrahydrofuran (40 ml). After a reaction time of 2.5 h the reaction was worked up as previously described and subjected to column chromatography on silica gel eluting with 2% ethanol in chloroform to afford a colourless oil (438 mg) which was converted to the HCl salt and crystallised to afford the title compound as a white solid. m.p. 222° C. dec. (from methanol-diethyl ether).

$^1$H Nmr (DMSO-d$_6$) δ:2.65 (3H, s), 3.29(2H, m), 3.88 (2H, s), 4.07 (1H, q, J=7Hz), 5.88 (1H, d, J=7Hz), 7.04–7.47 (13H, m), 9.48 (2H, br. s).

EXAMPLE 20

(±) trans 1-(2-Benzylanilino)-2-methylamino-1,2,3,4-tetrahydronaphthalene Hydrochloride (E20)

(±) trans 1-(2-Benzylanilino)-2-ethoxycarbonylaminoindane (2.47 g, 6.2 mmol) was reduced with LiAlH$_4$ (1.18 g, 31.0 mmol) as described for Example 2 employing a reaction time of 18 h. The reaction was worked up as described for Example 2. Crystallisation from diethyl ether/n-pentane afforded a colourless solid (1.52 g) which was treated with ethereal hydrogen chloride to give the title compound as a colourless solid, m.p. 178°–180° C. (from acetone/diethyl ether).

$^1$H Nmr (DMSO-d$_6$) δ:2.15 (1H, m), 2.32 (1H, m), 2.64 (3H, s), 3.00 (2H, m), 3.63 (1H, m), 4.03 (2H, ABq, J=17Hz), 5.13 (1H, t, J=8Hz), 5.52 (1H, d, J=8Hz), 6.68 (1H, t, J=7Hz), 6.88–7.48 (12H, m), 9.25 (2H, br s).

EXAMPLE 21

(±) cis 2-Amino-1-(4cyanophenoxy)indane Hydrochloride (E21)

A solution of (±) cis 2-amino-1-indanol (0.745 g, 5.0 mmol) in dry dimethyl sulfoxide (15 ml), was treated with sodium hydride (0.18 g of an 80% dispersion in oil; 6.0 mmol). After stirring for 3 h at room temperature under argon 4-fluorobenzonitrile (0.73 g, 6.0 mmol) was added in one portion. The mixture was warmed slowly to 40°–50° C. and held at this temperature for 2 h. The reaction was quenched at ice temperature with glacial acetic acid (0.34 ml, 6.0 mmol) and then concentrated in vacuo using co-distillation with xylene. The residue was partitioned between water (30 ml) and diethyl ether (60 ml). The aqueous layer was basified with potassium carbonate and further extracted with diethyl ether (4×60 ml). The combined organic layers were dried over $Na_2SO_4$ and then concentrated in vacuo. Purification by chromatography on silica gel eluting with 5–7.5% ethanol in diethyl ether afforded an oil (1.28 g). Extraction into a mixture of pentane and diethyl ether followed treatment with ethereal HCl afforded the hydrochloride salt which was recrystallised to give the title compound as a colourless solid (1.14 g), m.p. 230°–231° C. (from methanoildiethyl ether).

$^1$H Nmr (DMSO-$d_6$) δ:3.38 (2H,m), 4.30 (1H, q, J=6Hz), 6.18 (1H, d, J=6Hz), 7.30–7.63 (4H, m), 7.94 (2H, d, J=7Hz), 8.83 (3H, br s).

EXAMPLE 22

(±) cis 1-(4-Cyanophenoxy)-2-methylaminoindane Hydrochloride (E22)

The title compound was prepared in a similar manner to Example 21 from (±) cis 2-methylamino-1-indanol (0.815 g, 5.0 mmol), sodium hydride (0.18 g of an 80% dispersion in oil; 6.0 mmol) and 4-fluorobenzonitrile (0.73 g, 6.0 mmol). The crude product was purified by chromatography on silica eluting with 0–4% ethanol in diethyl ether. Extraction of the resulting pale brown oil (1.33 g) into a mixture of pentane and diethyl ether followed by treatment with ethereal HCl afforded the hydrochloride salt which was recrystallised to give the title compound as a colourless solid (1.15 g), m.p. 221°–223° C. (from methanol/acetone/diethyl ether).

$^1$H Nmr (DMSO-$d_6$) δ:2.67 (3H, s), 3.38 (2H, m), 4.13 (1H, m), 6.15 (1H, d, J=6Hz), 7.20–7.55 (6H, m), 7.83 (2H, d, J=7Hz), 9.68 (2H, br s).

EXAMPLE 23

(±) cis 2-Methylamino-1-(4-trifluoromethylphenoxy)indane Hydrochloride (E23)

The title compound was prepared in a similar manner to Example 21 from (±) cis 2-methylamino-1-indanol (0.49 g, 3.0 mmol), sodium hydride (0.11 g of an 80% dispersion in oil; 3.6 mmol) and 4-fluorobenzotrifluoride (0.59 g, 3.6 mmol). The crude product was purified by chromatography on silica eluting with 0–2% ethanol in diethyl ether. The resulting pale brown oil (0.77 g) was dissolved in a mixture of hexane and diethyl ether and treated with ethereal HCl to give the hydrochloride salt. Recrystallisation afforded the title compound as a colourless solid (0.7 g), m.p. 221°–223° C. (from methanol/acetone/diethyl ether).

$^1$H Nmr (DMSO-$d_6$) δ:2.78 (3H, s), 3.47 (2H, m), 4.23 (1H, m), 6.22 (1H, d, J=6Hz), 7.30–7.65 (6H, m), 7.82 (2H, d, J=7.5Hz), 9.80 (2H, br s).

EXAMPLE 24

(±) cis-1-Phenoxy-2-methylaminoindane Hydrochloride (E24)

The title compound was prepared in a similar manner to Example 12 from LiAlH$_4$ (250 mg, 6.5 mmol), (±) cis-1-phenoxy-2-tert-butoxycarbonylaminoindane (425 mg, 1.3 mmol) and tetrahydrofuran (30 ml). After a reaction time of 2 h the reaction was worked up as previously described and subjected to column chromatography on silica gel eluting with 5% ethanol in chloroform to afford a colourless oil (290 mg) which was converted to the HCl salt and crystallised to afford the title compound as a white solid. m.p. >215° C. dec. (from methanol-diethyl ether).

$^1$H Nmr (DMSO-$d_6$) δ:2.72 (3H, s), 3.40 (2H, m), 4.15 (1H, m), 6.00 (1H, d, J=6Hz), 7.06 (1H, t, J=7Hz), 7.27 (2H, m), 7.41 (5H, m), 9.54 (2H, br. s).

EXAMPLE 25

(±) cis 2-Amino-1-(4-trifluoromethylphenoxy) indane Hydrochloride (E25)

The title compound was prepared in a similar manner to Example 21 from (±) cis 2-amino-1-indanol (0.45 g, 3.0 mmol), sodium hydride (0.11 g of an 80% dispersion in oil; 3.6 mmol) and 4-fluorobenzotrifluoride (0.59 g, 3.6 mmol). The crude product was purified by chromatography on silica eluting with 0–2% ethanol in diethyl ether. The resulting oil (0.49 g) was dissolved in a mixture of hexane and diethyl ether and treated with ethereal HCl to give the hydrochloride salt. Recrystallisation afforded the title compound as a colourless solid (0.44 g), m.p. 231° C. (dec) (from ethyl acetate/diethyl ether).

$^1$H Nmr (DMSO-$d_6$) δ:3.33 (2H, m), 4.28 (1H, q, J=6Hz), 6.14 (1H, d, J=6Hz), 7.30–7.62 (6H, m), 7.80 (2H, d, J=7Hz), 8.67 (3H, br s).

EXAMPLE 26

(±) cis 2-Amino-1-(4Benzoylphenoxy)indane Hydrochloride (E26)

The title compound was prepared in a similar manner to Example 21 from (±) cis 2-amino-1-indanol (0.20 g, 1.34 mmol), sodium hydride (48 mg of an 80% dispersion in oil; 1.61 mmol) and 4-fluorobenzophenone (0.32 g, 1.61 mmol). The crude product was purified by chromatography on silica eluting with 0–5% ethanol in diethyl ether. The resulting orange oil (0.34 g) was extracted into pentane and treated with ethereal HCl to give the hydrochloride salt. Recrystallisation afforded the title compound as a colourless solid, m.p. 175° C. (dec) (from methanol/diethyl ether).

$^1$H Nmr (DMSO-$d_6$) δ:3.30 (2H, m), 4.20 (1H, m), 6.08 (1H, d, J=6Hz), 7.15–7.95 (13H, m), 8.70 (3H, br s).

EXAMPLE 27

(±) cis 1-(4-Benzoylphenoxy)-2-methylaminoindane Hydrochloride (E27)

A solution of (±) cis 2-methylamino-1-indanol (0.34 g, 2.1 mmol) in dry dimethyl sulfoxide (15 ml) was treated with sodium hydride (75 mg of an 80% dispersion in oil; 2.5 mmol). After stirring for 2.5 h at room temperature under argon 4-fluorobenzophenone (0.50 g, 2.5 mmol) was added in one portion. The mixture was stirred overnight at room temperature and then worked up as described in Example 21. The crude product was purified by chromatography on silica eluting with 0–4% ethanol in diethyl ether. The resulting pale brown oil (0.61 g) was extracted into a mixture of hexane and diethyl ether and treated with ethereal HCl to give the hydrochloride salt. Recrystallisation afforded the title compound as a colourless solid (0.53 g), m.p. 225° C. (dec) (from methanol/acetone/diethyl ether).

¹H Nmr (CDCl₃) δ:2.72 (3H, s), 3.40 (1H, dd, J=15Hz and J=7Hz), 3.58 (1H, dd, J=15Hz and J=7Hz), 3.93 (1H, m), 6.00 (1H, d, J=6Hz), 7.10–7.88 (13H, m), 10.18 (2H, br s).

EXAMPLES 28 and 29

(+)cis-1-(4-Benzyloxyphenoxy)-2-methylaminoindane Hydrochloride (E28)

(−)cis-1-(4-Benzyloxyphenoxy)-2-methylaminoindane Hydrochloride (E29)

To a solution of S-(+)-α-methoxyphenylacetic acid (5 g, 30 mmol) in dichloromethane (250 ml) was added thionyl chloride (37.5 ml) and the mixture heated at reflux for 90 minutes. On cooling, the mixture was concentrated in vacuo. The residue was then dissolved in dichloromethane (125 ml) and added to a mixture of (±)cis-1-(4-benzyloxyphenoxy)-2-methylaminoindane (10.29 g, 30 mmol), dichloromethane (125 ml) and 1M aq. sodium hydroxide (250 ml). The two phase mixture was then stirred vigorously for 1 h. The layers were then separated and the aqueous phase extracted with dichloromethane. The combined organic phases were washed with brine, dried over sodium sulfate and concentrated in vacuo to afford a 50:50 mixture of two diastereomers which were readily separated by column chromatography on silica gel, eluting with 50% ether in petrol. The more polar diastereomer (7 g, 14 mmol) was then dissolved in dry tetrahydrofuran (150 ml) under argon and treated with methyl lithium (1.4M in diethyl ether, 40 ml, 57 mmol). After 30 minutes at room temperature the reaction was queched with glacial acetic acid (5 ml), poured into aqueous potassium carbonate (500 ml) and extracted with diethyl ether. The combined organic extracts were dried over sodium sulfate and concentrated in vacuo. The residue was subjected to column chromatography on silica gel eluting with 5% ethanol in chloroform to afford a brown oil (1.51 g) which was converted to the HCl salt and crystallised to afford (−)-cis-1-(4-benzyloxyphenoxy)-2-methylaminoindane hydrochloride as a white solid. m.p. >220° C. dec. (from methanoldiethyl ether).

Specific optical rotation=−178° (chloroform, c=1, 20° C.)

The less polar diastereomer (6.5 g, 13 mmol) was then dissolved in dry tetrahydrofuran and treated with potassium tert-butoxide (65 g), and water (1.1 ml). The mixture was then stirred vigorously for 90 minutes. After filtering off the solid material, the mixture was poured into water (400 ml) and extracted with diethyl ether. The combined organic extracts were dried over sodium sulfate and concentrated in vacuo to afford a yellow oil which was converted to the HCl salt and crystallised to afford (+) cis-1-(4-benzyloxyphenoxy)- 2-methylaminoindane hydrochloride (3 g) as a white solid. m.p. >205° C. dec. (from methanol-diethyl ether).

Specific optical rotation=+177° (chloroform, c=1, 20° C.)

EXAMPLE 30

(±) cis 2-Amino-1-(3,4dichlorophenoxy)indane Hydrochloride (E30)

The title compound was prepared in a similar manner to Example 26 from (±) cis 2-amino-1-indanol (2.24 g, 15.0 mmol), sodium hydride (0.54 g of an 80% dispersion in oil; 18.0 mmol) and 1,2-dichloro-4-fluorobenzene (2.97 g, 18.0 mmol). The crude product was purified by chromatography on silica eluting with 0–4% ethanol in diethyl ether. The resulting light brown oil (3.89 g) was extracted into a mixture of hexane and diethyl ether and treated with ethereal HCl to give the hydrochloride salt. Recrystallisation afforded the title compound as a colourless solid, m.p. 214°–215° C. (dec) (from methanol/ethyl acetate/diethyl ether).

¹H Nmr (DMSO-d₆) δ:3.23 (2H, m), 4.15 (1H, m), 5.91 (1H, d, J=6Hz), 7.15–7.60 (7H, m), 8.48 (3H, br s).

EXAMPLE 31

(±) cis 1-(3,4-Dichlorophenoxy)-2-dimethylaminoindane Hydrochloride (E31)

A solution of (±) cis 2-amino-1-(3,4dichlorophenoxy) indane (0.88 g, 3.0 mmol) in acetonitrile (40 ml) was treated with formaldehyde (2 ml of a 37% aqueous solution, 26 mmol) followed by sodium cyanoborohydride (0.38 g, 6.0 mmol). The mixture was stirred at room temperature for 6 days while maintaining the pH at 5–7 by the addition of glacial acetic acid. The reaction mixture was diluted with diethyl ether and washed with 1M sodium hydroxide followed by brine. The organic layer was dried over Na₂SO₄ and concentrated in vacuo. Passage through a short column of neutral alumina eluting with 0.5–1% ethanol in chloroform afforded a colourless oil which was converted into the hydrochloride salt and recrystallised to give the title compound as a colourless solid (0.6 g), m.p. 219°–220° C. (from methanol/ethyl acetate/diethyl ether).

¹H Nmr (DMSO-d₆) δ:2.90 and 2.95 (each 3H, d, J=2Hz, protomers), 3.45 (2H, m), 4.25 (1H, m), 6.16 (1H, d, J=6Hz), 7.20–7.70 (7H, m), 10.91 1H, br s).

EXAMPLE 32

(±) cis 1-(3,4-Dichlorophenoxy)-2-methylaminoindane Hydrochloride (E32)

The title compound was prepared in a similar manner to Example 26 from (±) cis 2-methylamino-1-indanol (0.815 g, 5.0 mmol), sodium hydride (0.18 g of an 80% dispersion in oil; 6.0 mmol) and 1,2-dichloro-4-fluorobenzene (0.99 g, 6.0 mmol). The crude product was purified by chromatography on silica eluting with 0–3% ethanol in diethyl ether. The resulting brown oil (1.3 g) was dissolved in hexane and treated with ethereal HCl to give the hydrochloride salt. Recrystallisation afforded the title compound as a colourless solid, m.p. 238°–239° C. (dec) (from methanoildiethyl ether).

¹H Nmr (DMSO-d₆) δ:2.65 (3H, s), 3.31 (2H,m), 4.10 (1H, m), 6.02 (1H, d, J=6Hz), 7.20–7.65 (7H, m), 9.65 (2H,br s).

EXAMPLE 33

(±) cis 1-[4-(4Fluorophenoxy)phenoxy]-2-methylandnoindane Hydrochloride (E33)

A solution of (±) cis 2-methylamino-1-indanol (0.815 g, 5.0 mmol) in dry dimethyl sulfoxide (20 ml) was treated with sodium hydride (0.18 g of an 80% dispersion in oil; 6.0 mmol). After stirring for 3 h at room temperature under argon bis-(4-fluorophenyl)-ether (2.06 g, 10.0 mmol) was added and the mixture was heated at 60° C. for 18 h. The reaction was worked up as described in Example 21 and the crude product was purified by chromatography on silica eluting with 0–4% ethanol in diethyl ether. The resulting light brown oil (0.78 g) was extracted into hexane and treated with ethereal HCl to give the hydrochloride salt. Recrystallisation afforded the title compound as a colourless solid (0.67 g), m.p. 198°–200° C. (from methanol/acetone/diethyl ether).

¹H Nmr (DMSO-d₆) δ:2.70 (3H, s), 3.35 (2H, m), 4.10 (1H, m), 5.88 (1H, d, J=6Hz), 6.90–7.50 (12H, m), 9.60 (1H, br s).

EXAMPLE 34

(±)cis-1-(4-Phenylphenoxy)-2-methylaminoindane Hydrochloride (E34)

To a solution of LiAlH₄ (1.39 g, 37 mmol) in dry tetrahydrofuran (50 ml) under argon was added dropwise a solution of (±)cis-1-(4-phenylphenoxy)-2-tert-butoxycarbonylaminoindane (2.38 g, 6 mmol) in dry tetrahydrofuran (100 ml). The reaction was heated at reflux for 2 h then cooled with an ice/water bath and quenched with the minimum of water. The reaction was filtered and dried over MgSO₄. Solvents were removed in vacuo and the residue subjected to column chromatography on silica gel eluting with 5% ethanol in chloroform to afford a colourless oil (980 mg), which was converted to the HCl salt and crystallised to afford the title compound as a white solid. m.p. >242° C. dec. (from methanol-diethyl ether).

¹H Nmr (CDCl₃) δ:2.75 (3H,s), 3.41 (2H, m), 4.20 (1H, q, J=7Hz), 6.09 (1H, d, J=7Hz), 7.30–7.55 (9H, m), 7.72 (4H, m), 9.68 (2H, br.s).

EXAMPLE 35

(±)cis-1-(3-Phenylphenoxy)-2-methylaminoindane Hydrochloride (E35)

To a solution of LiAlH₄ (1.53 g, 40 mmol) in dry tetrahydrofuran (50 ml) under argon was added dropwise a solution of (±)cis-1-(3-phenylphenoxy)-2-tert-butoxycarbonylaminoindane (3.08 g, 8 mmol) in dry tetrahydrofuran (150 ml). The reaction was heated at reflux for 3 h then cooled with an ice/water bath and quenched with the minimum of water. The reaction was filtered and dried over MgSO₄. Solvents were removed in vacuo and the residue subjected to column chromatography on silica gel eluting with 5% ethanol in chloroform to afford a colourless oil (1.38 g,) which was converted to the HCl salt and crystallised to afford the title compound as a white solid. m.p. >185° C. dec. (from methanol-diethyl ether).

¹H Nmr (CDCl₃) δ:2.68 (3H, s), 3.26–3.43 (2H, m), 4.13 (1H, q, J=7Hz), 6.07 (1H, d, J=7Hz), 7.25 (2H, t, J=7Hz), 7.33–7.51 (9H, m), 7.70 (2H, d, J=7Hz), 9.57 (2H, br.s).

EXAMPLE 36

(±)cis-1-(4-tert-Butylphenoxy)-2-methylaminoindane Hydrochloride (E36)

To a solution of LiAlH₄ (730 mg, 19 mmol) in dry tetrahydrofuran (30 ml) under argon was added dropwise a solution of (±)cis-1-(4-tert-butylphenoxy)-2-tert-butoxycarbonylaminoindane (1.4 g, 3.7 mmol) in dry tetrahydrofuran (60 ml). The reaction was heated at reflux for 3 h then cooled with an ice/water bath and quenched with the minimum of water. The reaction was filtered and dried over MgSO₄. Solvents were removed in vacuo and the residue subjected to column chromatography on silica gel eluting with 5% ethanol in chloroform to afford a colourless oil (618 mg,) which was converted to the HCl salt and crystallised to afford the title compound as a white solid. m.p. >218° C. dec. (from methanol-diethyl ether).

¹H Nmr (CDCl₃) δ:1.26 (9H, s), 2.64 (3H, s), 3.27–3.33 (2H, m), 4.08 (1H, q, J=7Hz), 5.99 (1H, d, J=7Hz), 7.13 (2H, d, J=9Hz), 7.23 (1H, m), 7.32–7.40 (5H, m), 9.49 (2H, br.s).

EXAMPLE 37

(±) cis-2-Amino-1-[4-(4-fluorophenoxy)phenoxy)] indane Hydrochloride (E37)

A solution of (±) cis-2-amino-1-indanol (0.745 g, 5.0 mmol) in dry dimethyl sulfoxide (20 ml) was treated with sodium hydride (0.18 g of an 80% dispersion in oil; 6.0 mmol). After stirring for 3 h at room temperature under argon bis-(4-fluorophenyl)-ether (2.06 g, 10.0 mmol) was added in one portion. The mixture was heated at 60° C. for 24 h. After quenching with glacial acetic acid (0.32 ml) the reaction was worked up as described in Example 21. The crude product was purified by chromatography on silica eluting with 0–5% ethanol in diethyl ether. The resulting dark oil was extracted into a mixture of hexane and diethyl ether and insoluble impurities were removed by filtration. The filtrate was treated with ethereal HCl to give the hydrochloride salt. Recrystallisation afforded the title compound as a colourless solid (0.69 g), m.p. 225° C. (dec) (from methanol/acetone/diethyl ether).

¹H Nmr (DMSO-d₆) δ:3.23 (2H, m), 4.13 (1H, q, J=7Hz), 5.78 (1H, d, J=7Hz), 7.00 (4H, m), 7.20 (5H, m), 7.38 (3H, m), 8.65 (3H, br s).

EXAMPLE 38

(±) cis-2-Amino-1-[4-(4-fluorobenzoyl)phenoxy] indane Hydrochloride (E38)

A solution of (±) cis-2-amino-1-indanol (0.745 g, 5.0 mmol) in dry dimethyl sulfoxide (20 ml) was treated with sodium hydride (0.18 g of an 80% dispersion in oil; 6.0 mmol). After stirring for 2.5 h at room temperature under argon 4,4'-difluorobenzophenone (1.31 g, 6.0 mmol) was added in one portion. The mixture was stirred overnight at room temperature. After quenching with glacial acetic acid (0.32 ml) the reaction was worked up as described in Example 21. The crude product was purified by chromatography on silica eluting with 0–5% ethanol in diethyl ether. The resulting oil (1.0 g) was extracted into a mixture of hexane and diethyl ether and insoluble impurities were removed by filtration. The filtrate was treated with ethereal HCl to give the hydrochloride salt. Recrystallisation afforded the title compound as a colourless solid (0.97 g), m.p. 119°–122° C. (from methanol/diethyl ether).

¹H Nmr (DMSO-d₆) δ:3.28 (2H, m), 4.20 (1H, q, J=7Hz), 6.10 (1H, d, J=7Hz), 7.20–7.58 (8H, m), 7.80 (4H, m), 8.70 (3H, br s).

EXAMPLE 39

(±) cis-1-[4-(4-Fluorobenzoyl)phenoxy]-2-methylaminoindane Hydrochloride (E39)

A solution of (±) cis 2-methylamino-1-indanol (0.815 g, 5.0 mmol) in dry dimethyl sulfoxide (20 ml) was treated with sodium hydride (0.18 g of an 80% dispersion in oil; 6.0 mmol). After stirring for 2.5 h at room temperature under argon 4,4'-difluorobenzophenone (1.31 g, 6.0 mmol) was added in one portion. The mixture was stirred overnight at room temperature. After quenching with glacial acetic acid (0.32 ml) the reaction was worked up as described in Example 21. The crude product was purified by chromatography on silica eluting with 0–5% ethanol in diethyl ether. The resulting oil was extracted into a mixture of hexane and diethyl ether and insoluble impurities were removed by filtration. The filtrate was treated with ethereal HCl to give the hydrochloride salt. Recrystallisation afforded the title compound as a colourless solid, m.p. 229°–230° C. (dec.) (from methanol/diethyl ether).

$^1$H Nmr (DMSO-d$_6$) δ:2.66 (3H, s), 3.32 (2H, m), 4.12 (1H, br. m), 6.15 (1H, d, J=7Hz), 7.25 (1H, m), 7.40 (6H, m), 7.58 (1H, d, J=7Hz), 7.82 (4H, m).

EXAMPLE 40

(±) cis-1-[4-(4-Fluorophenoxy)phenoxy]-2-isopropylaminoindane (E40)

The title compound was prepared in a similar manner to Example 31 from (±) cis-2-amino-1-[4-(4-fluorophenoxy) phenoxy]indane (70 mg, 0.2 mmol), sodium cyanoborohydride (25 mg, 0.4 mmol), acetone (0.29 ml, 4 mmol) and acetonitrile (10 ml). After subjecting the crude product to column chromatography on silica gel eluting with 5% ethanol in chloroform, residual boron impurities were removed by dissolving the product in hexanes and filtering. Removal of the hexanes in vacuo afforded the title compound (40 mg) as a colourless oil.

$^1$H Nmr (CDCl$_3$) δ:1.05 (3H, d, J=6Hz), 1.13 (3H, d, J=6Hz), 1.85 (1H, br. s), 3.00 (2H, m), 3.15 (1H, dd, J=7,15Hz)3.71 (1H, m), 5.46 (1H, d, J=5Hz), 6.86–7.42 (12H, m).

We claim:

1. Method of treatment of a condition or disease related to the accumulation of calcium in the brain cells of a mammal which comprises administering to a subject in need thereof an effective amount of a compound of formula (I):

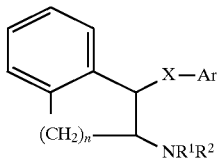

Formula (I)

wherein

X represents O, S or NH;

R$^1$ and R$^2$ each independently represent hydrogen, C$_{1-6}$alkyl, C$_{3-6}$cycloalkyl, or C$_{1-4}$alkyl-C$_{3-6}$cycloalkyl;

n is 1, 2 or 3; and

Ar represents an phenyl optionally substituted by 1 to 3 substituents selected from:

halo, C$_{1-4}$alkyl, C$_{1-4}$alkoxy, C$_{1-2}$alkylenedioxy, trifluoromethyl, trifluoromethoxy, CN, NO$_2$, amino, mono- or di-alkylamino, optionally substituted benzoyl and Ph(CH$_2$)$_r$Y(CH$_2$)$_s$— where Ph is optionally substituted phenyl, Y is oxygen or a bond and r and s each independently represent 0–4 provided that the sum of r+s is not greater than 4, or Ar represents an optionally substituted unsaturated monocyclic heteroaryl ring system containing 5 or 6 ring members, or an optionally substituted, unsaturated or partially saturated bicyclic aryl or heteroaryl ring system containing 8–10 ring members, or a pharmaceutically acceptable salt thereof.

2. The method of treatment according to claim 1 wherein the disorder is a condition or disease related to an accumulation of calcium in the brain cells of a mammal.

3. A method of treatment according to claim 1 in which the compound of formula (I) is in the form of a resolved enantiomer, substantially free from the other enantiomer.

4. A compound of formula (IA):

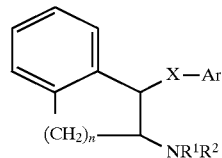

Formula (IA)

wherein

X represents O, S or NH;

R$^1$ and R$^2$ each independently represent hydrogen, C$_{1-6}$alkyl, C$_{3-6}$cycloalkyl, or C$_{1-4}$alkyl-C$_{3-6}$cycloalkyl;

n is 1, 2 or 3; and

Ar represents phenyl optionally substituted by 1 to 3 substituents selected from:

halo, C$_{1-4}$alkyl, C$_{1-4}$alkoxy, C$_{1-2}$alkylenedioxy, trifluoromethyl, trifluoromethoxy, CN, NO$_2$, amino, mono- or di- alkylamino, optionally substituted benzoyl and Ph(CH$_2$)$_r$Y(CH$_2$)$_s$— where Ph is optionally substituted phenyl, Y is oxygen or a bond and r and s each independently represent 0–4 provided that the sum of r+s is not greater than 4, or Ar represents an optionally substituted unsaturated monocyclic heteroaryl ring system containing 5 or 6 ring members, or an optionally substituted, unsaturated or partially saturated bicyclic aryl or heteroaryl ring system containing 8–10 ring members, with the proviso that when X is O or S then Ar is not an unsubstituted phenyl group or phenyl substituted by lower alkyl, lower alkoxy, trifluoromethyl or halogen;

or a salt thereof.

5. A compound according to claim 4 wherein Ar represents phenyl substituted by optionally substituted benzoyl or a group Ph(CH$_2$)$_r$Y(CH$_2$)$_s$—.

6. A compound according to claim 5 wherein r and s independently represent zero or 1, such that the sum of r and s does not exceed 1.

7. A compound according to claim 4 wherein n represents 1 or 2.

8. A compound according to claim 4 wherein at least one of R$^1$ and R$^2$ represents C$_{1-6}$alkyl.

9. A compound according to claim 4 wherein R$^1$ is methyl or isopropyl.

10. A compound according to claim 4 wherein R$^2$ is hydrogen.

11. A compound according to claim 4 wherein X is O.

12. A compound according to claim 4 in which the optionally substituted benzoyl group or the Ph(CH$_2$)$_r$Y (CH$_2$)$_s$— group is in the 4-position.

13. A compound according to claim 4 wherein Ph(CH$_2$)$_r$Y(CH$_2$)$_s$— is optionally substituted benzyloxy, benzyl, or phenoxy, where the optional substituents are halogen, C$_{1-4}$alkoxy, C$_{1-4}$alkyl, trifluoromethyl or trifluoromethoxy.

14. A compound according to claim 4 wherein the substituents on optionally substituted benzoyl, benzyloxy, benzyl, or phenoxy is 4-fluoro, 4-chloro, 3-fluoro, 3-chloro or 3,4-dichloro.

15. A compound according to claim 4 in the form of a resolved enantiomer, substantially free from the other enantiomer.

16. A compound of formula (I) claim 4 selected from:

(±) trans 1-(2-benzylanilino)-2-methylaminoindane,
(±)cis-1-(4-benzyloxyphenoxy)-2-methylaminoindane,
(+)cis-1-(4-benzyloxyphenoxy)-2-methylaminoindane,
(−)cis-1-(4-benzyloxyphenoxy)-2-methylaminoindane, (±)cis-1-[(4-phenoxy)phenoxy]-2-methylaminoindane,
(±)trans-1-(4-benzyloxyphenoxy)-2-methylaminoindane,
(±)cis-1-(4-benzylphenoxy)-2-n-ethylaminoindane,
(±) cis 2-amino-1-(4-benzoylphenoxy)indane,
(±) cis 1-(4-benzoylphenoxy)-2-methylaminoindane,
(±) cis 1-[4-(4-fluorophenoxy)phenoxy]-2-methylaminoindane,
(±)cis-1-(4-phenylphenoxy)-2-methylaminoindane,
(±)cis-1-(3-phenylphenoxy)-2-methylaminoindane,
(±) cis 2-amino-1-[4-(4-fluorophenoxy)phenoxy]indane,
(±) cis-2-amino-1-[4-(4-fluorobenzoyl)phenoxy]indane,
(±) cis-1-[4-(4-fluorobenzoyl)phenoxy]-2-methylamninoindane,
(±) cis 1-[4-(4-fluorophenoxy)phenoxy]-2-isopropylaminoindane, or a salt thereof.

17. A pharmaceutical composition comprising a compound of claim 4 or a pharmaceutically acceptable salt thereof and a pharmaceutically acceptable carrier or excipient.

* * * * *